(12) United States Patent
Torres et al.

(10) Patent No.: US 8,846,609 B2
(45) Date of Patent: Sep. 30, 2014

(54) LEUKOTOXIN E/D AS A NEW ANTI-INFLAMMATORY AGENT AND MICROBICIDE

(75) Inventors: Victor J. Torres, New York, NY (US); Derya Unutmaz, New York, NY (US); Francis Alonzo, III, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/527,438

(22) Filed: Jun. 19, 2012

(65) Prior Publication Data

US 2013/0039885 A1 Feb. 14, 2013

Related U.S. Application Data

(60) Provisional application No. 61/498,606, filed on Jun. 19, 2011.

(51) Int. Cl.
| | | |
|---|---|---|
| A01N 37/18 | (2006.01) | |
| A61K 38/04 | (2006.01) | |
| A61P 31/12 | (2006.01) | |
| A01N 43/42 | (2006.01) | |
| A61K 31/44 | (2006.01) | |
| A61K 31/497 | (2006.01) | |
| A61K 39/395 | (2006.01) | |
| A61K 38/16 | (2006.01) | |

(52) U.S. Cl.
CPC ................................. *A61K 38/164* (2013.01)
USPC ............... 514/2.7; 514/2.4; 514/2.6; 514/3.7; 514/304; 514/459; 514/252.18; 424/143.1; 424/145.1

(58) Field of Classification Search
None
See application file for complete search history.

(56) References Cited

U.S. PATENT DOCUMENTS

| | | |
|---|---|---|
| 2003/0171563 A1 | 9/2003 | McNamara |
| 2005/0287167 A1 | 12/2005 | zur Megede et al. |
| 2008/0131457 A1 | 6/2008 | Taylor et al. |
| 2009/0053235 A1 | 2/2009 | Taylor et al. |
| 2009/0247570 A1* | 10/2009 | Mayer ............................ 514/303 |
| 2010/0284909 A1 | 11/2010 | Wisniewski et al. |
| 2011/0143992 A1* | 6/2011 | Taub et al. ...................... 514/1.4 |

FOREIGN PATENT DOCUMENTS

| | | |
|---|---|---|
| WO | 2007062150 A2 | 5/2007 |
| WO | 2010/119343 A2 | 10/2010 |
| WO | 2011047011 A2 | 4/2011 |

OTHER PUBLICATIONS

Alonzo et al., Nature (2013), vol. 493, pp. 51-57.*
International Search Report and Written Opinion for PCT International Patent Application No. PCT/US12/43182 (mailed Dec. 13, 2012).
Vyas et al., "Recurrent Community-Acquired Methicillin-Resistant *Staphylococcus aureus* Infections in an HIV-Infected Person," J. Clin. Microbiol. 49(5):2047-2053 (2011).
Kuroda et al., UniProt Accession No. Q99T53, dated Nov. 30, 2010 (retrieved Nov. 29, 2012).
Kuroda et al., UniProt Accession No. Q99T54, dated Nov. 30, 2010 (retrieved Nov. 29, 2012).
Tumang et al., "T Helper Cell-Dependent, Microbial Superantigen-Induced Murine B Cell Activation: Polyclonal and Antigen-Specific Antibody Responses," J. Immunol. 147(2):432-438 (1991).
Lin et al., "New Insights Into the Prevention of *Staphylococcal* Infections and Toxic Shock Syndrome," Expert Rev. Clin. Pharmacol. 3(6):753-767 (2010).
Ashorn et al., "Elimination of Infectious Human Immunodeficiency Virus from Human T-Cell Cultures by Synergistic Action of CD4-Pseudomonas Exotoxin and Reverse Transcriptase Inhibitors," Proc. Natl. Acad. Sci. USA 87:8889-8893 (1990).
Chavakis et al., "The Anti-Inflammatory Activites of *Staphylococcus aureus*," Trends Immunol. 28(9):408-418 (2007).
International Search Report and Written Opinion for PCT International Patent Application No. PCT/US12/43179 (mailed Dec. 10, 2012).
Ward et al., UniProt Accession No. C8L2Y6, dated Mar. 8, 2011 (retrieved Nov. 20, 2012).
Gravet et al., "Characterization of a Novel Structural Member, LukE-LukD, of the Bi-Component *Staphylococcal* Leucotoxins Family," FEBS Lett. 436:202-208 (1998).
Keppler et al., "Progress Toward a Human CD4/CCR5 Transgenic Rat Model for De Novo Infection by Human Immunodeficiency Virus Type 1," J. Exp. Med. 195(6):719-736 (2002).
McNamara et al., "A rot Mutation Restores Parental Virulence to an agr-Null *Staphylococcus aureus* Strain in a Rabbit Model of Endocarditis," Infect. & Immun. 73(6):3806-3809 (2005).
McNamara et al., "Identification, Cloning, and Initial Characterization of rot, a Locus Encoding a Regulator of Virulence Factor Expression in *Staphylococcus aureus*," J. Bacteriol. 182(11)3197-3203 (2000).

* cited by examiner

*Primary Examiner* — Christine J Saoud
*Assistant Examiner* — Jegatheesan Seharaseyon
(74) *Attorney, Agent, or Firm* — LeClairRyan, a Professional Corporation

(57) ABSTRACT

The present invention relates to methods for preventing or treating Human Immunodeficiency Virus (HIV) infection, inflammatory conditions, and graft-versus-host-disease (GVHD) in a subject. Therapeutic compositions of the present invention comprise Leukocidin E (LukE) and/or D proteins or polypeptides. The invention further relates to methods of treating *Staphylococcus aureus* infection by administering a composition comprising a CCR5 antagonist or any molecule that blocks LukE/D interaction with CCR5+ cells in an amount effective to treat the *S. aureus* infection in the subject.

5 Claims, 6 Drawing Sheets

SEQUENCE LISTING

```
<160> NUMBER OF SEQ ID NOS: 22

<210> SEQ ID NO 1
<211> LENGTH: 311
<212> TYPE: PRT
<213> ORGANISM: Staphylococcus aureus

<400> SEQUENCE: 1

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
```

```
                65                  70                  75                  80
        Phe Ile Asn Ser Arg Thr Ser Phe Ser Asp Val Lys Gly Ser Gly Tyr
                            85                  90                  95

Glu Leu Thr Lys Arg Met Ile Trp Pro Phe Gln Tyr Asn Ile Gly Leu
                        100                 105                 110

Thr Thr Lys Asp Pro Asn Val Ser Leu Ile Asn Tyr Leu Pro Lys Asn
                        115                 120                 125

Lys Ile Glu Thr Thr Asp Val Gly Gln Thr Leu Gly Tyr Asn Ile Gly
                    130                 135                 140

Gly Asn Phe Gln Ser Ala Pro Ser Ile Gly Gly Asn Gly Ser Phe Asn
        145                 150                 155                 160

Tyr Ser Lys Thr Ile Ser Tyr Thr Gln Lys Ser Tyr Val Ser Glu Val
                            165                 170                 175

Asp Lys Gln Asn Ser Lys Ser Val Lys Trp Gly Val Lys Ala Asn Glu
                        180                 185                 190

Phe Val Thr Pro Asp Gly Lys Lys Ser Ala His Asp Arg Tyr Leu Phe
                        195                 200                 205

Val Gln Ser Pro Asn Gly Pro Thr Gly Ser Ala Arg Glu Tyr Phe Ala
                    210                 215                 220

Pro Asp Asn Gln Leu Pro Leu Val Gln Ser Gly Phe Asn Pro Ser
        225                 230                 235                 240

Phe Ile Thr Thr Leu Ser His Glu Lys Gly Ser Ser Asp Thr Ser Glu
                            245                 250                 255

Phe Glu Ile Ser Tyr Gly Arg Asn Leu Asp Ile Thr Tyr Ala Thr Leu
                        260                 265                 270

Phe Pro Arg Thr Gly Ile Tyr Ala Glu Arg Lys His Asn Ala Phe Val
                        275                 280                 285

Asn Arg Asn Phe Val Val Arg Tyr Glu Val Asn Trp Lys Thr His Glu
                    290                 295                 300

Ile Lys Val Lys Gly His Asn
        305                 310

<210> SEQ ID NO 2
<211> LENGTH: 311
<212> TYPE: PRT
<213> ORGANISM: Staphylococcus aureus

<400> SEQUENCE: 2

Met Phe Lys Lys Lys Met Leu Ala Ala Thr Leu Ser Val Gly Leu Ile
        1               5                   10                  15

Ala Pro Leu Ala Ser Pro Ile Gln Glu Ser Arg Ala Asn Thr Asn Ile
                        20                  25                  30

Glu Asn Ile Gly Asp Gly Ala Glu Val Ile Lys Arg Thr Glu Asp Val
                    35                  40                  45

Ser Ser Lys Lys Trp Gly Val Thr Gln Asn Val Gln Phe Asp Phe Val
        50                  55                  60

Lys Asp Lys Lys Tyr Asn Lys Asp Ala Leu Ile Val Lys Met Gln Gly
        65                  70                  75                  80

Phe Ile Asn Ser Arg Thr Ser Phe Ser Asp Val Lys Gly Ser Gly Tyr
                            85                  90                  95

Glu Leu Thr Lys Arg Met Ile Trp Pro Phe Gln Tyr Asn Ile Gly Leu
                        100                 105                 110

Thr Thr Lys Asp Pro Asn Val Ser Leu Ile Asn Tyr Leu Pro Lys Asn
                        115                 120                 125
```

```
Lys Ile Glu Thr Thr Asp Val Gly Gln Thr Leu Gly Tyr Asn Ile Gly
            130                 135                 140
Gly Asn Phe Gln Ser Ala Pro Ser Ile Gly Gly Asn Gly Ser Phe Asn
145                 150                 155                 160
Tyr Ser Lys Thr Ile Ser Tyr Thr Gln Lys Ser Tyr Val Ser Glu Val
            165                 170                 175
Asp Lys Gln Asn Ser Lys Ser Val Lys Trp Gly Val Lys Ala Asn Glu
            180                 185                 190
Phe Val Thr Pro Asp Gly Lys Lys Ser Ala His Asp Arg Tyr Leu Phe
            195                 200                 205
Val Gln Ser Pro Asn Gly Pro Thr Gly Ser Ala Arg Glu Tyr Phe Ala
            210                 215                 220
Pro Asp Asn Gln Leu Pro Leu Val Gln Ser Gly Phe Asn Pro Ser
225                 230                 235                 240
Phe Ile Thr Thr Leu Ser His Glu Lys Gly Ser Ser Asp Thr Ser Glu
            245                 250                 255
Phe Glu Ile Ser Tyr Gly Arg Asn Leu Asp Ile Thr Tyr Ala Thr Leu
            260                 265                 270
Phe Pro Arg Thr Gly Ile Tyr Ala Glu Arg Lys His Asn Ala Phe Val
            275                 280                 285
Asn Arg Asn Phe Val Val Arg Tyr Glu Val Asn Trp Lys Thr His Glu
290                 295                 300
Ile Lys Val Lys Gly His Asn
305                 310

<210> SEQ ID NO 3
<211> LENGTH: 311
<212> TYPE: PRT
<213> ORGANISM: Staphylococcus aureus

<400> SEQUENCE: 3

Met Phe Lys Lys Lys Met Leu Ala Ala Thr Leu Ser Val Gly Leu Ile
1               5                   10                  15
Ala Pro Leu Ala Ser Pro Ile Gln Glu Ser Arg Ala Asn Thr Asn Ile
            20                  25                  30
Glu Asn Ile Gly Asp Gly Ala Glu Val Ile Lys Arg Thr Glu Asp Val
            35                  40                  45
Ser Ser Lys Lys Trp Gly Val Thr Gln Asn Val Gln Phe Asp Phe Val
            50                  55                  60
Lys Asp Lys Lys Tyr Asn Lys Asp Ala Leu Ile Val Lys Met Gln Gly
65                  70                  75                  80
Phe Ile Asn Ser Arg Thr Ser Phe Ser Asp Val Lys Gly Ser Gly Tyr
            85                  90                  95
Glu Leu Thr Lys Arg Met Ile Trp Pro Phe Gln Tyr Asn Ile Gly Leu
            100                 105                 110
Thr Thr Lys Asp Pro Asn Val Ser Leu Ile Asn Tyr Leu Pro Lys Asn
            115                 120                 125
Lys Ile Glu Thr Thr Asp Val Gly Gln Thr Leu Gly Tyr Asn Ile Gly
            130                 135                 140
Gly Asn Phe Gln Ser Ala Pro Ser Ile Gly Gly Asn Gly Ser Phe Asn
145                 150                 155                 160
Tyr Ser Lys Thr Ile Ser Tyr Thr Gln Lys Ser Tyr Val Ser Glu Val
            165                 170                 175
Asp Lys Gln Asn Ser Lys Ser Val Lys Trp Gly Val Lys Ala Asn Glu
            180                 185                 190
```

```
Phe Val Thr Pro Asp Gly Lys Lys Ser Ala His Asp Arg Tyr Leu Phe
            195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
            245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
            275                 280                 285

Asn Arg Asn Phe Val Val Arg Tyr Glu Val Asn Trp Lys Thr His Glu
            290                 295                 300

Ile Lys Val Lys Gly His Asn
305                 310

<210> SEQ ID NO 4
<211> LENGTH: 311
<212> TYPE: PRT
<213> ORGANISM: Staphylococcus aureus

<400> SEQUENCE: 4

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
            35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
            85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
            115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
            165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
            195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
```

```
            245                 250                 255
Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 5
<211> LENGTH: 311
<212> TYPE: PRT
<213> ORGANISM: Staphylococcus aureus

<400> SEQUENCE: 5

Met Phe Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300
```

```
Ile Lys Val Lys Gly His Asn
305                 310

<210> SEQ ID NO 6
<211> LENGTH: 311
<212> TYPE: PRT
<213> ORGANISM: Staphylococcus aureus

<400> SEQUENCE: 6

Met Phe Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
                35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
                115                 120                 125

Lys Ile Glu Thr Thr Asp Val Gly Gln Thr Leu Gly Tyr Asn Ile Gly
            130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 7
<211> LENGTH: 311
<212> TYPE: PRT
<213> ORGANISM: Staphylococcus aureus

<400> SEQUENCE: 7
```

```
Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
    275                 280                 285

Asn Arg Asn Phe Val Val Arg Tyr Glu Val Asn Trp Lys Thr His Glu
290                 295                 300

Ile Lys Val Lys Gly His Asn
305                 310

<210> SEQ ID NO 8
<211> LENGTH: 311
<212> TYPE: PRT
<213> ORGANISM: Staphylococcus aureus

<400> SEQUENCE: 8

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60
```

```
Lys Asp Lys Lys Tyr Asn Lys Asp Ala Leu Ile Val Lys Met Gln Gly
 65                  70                  75                  80

Phe Ile Asn Ser Arg Thr Ser Phe Ser Asp Val Lys Gly Ser Gly Tyr
                 85                  90                  95

Glu Leu Thr Lys Arg Met Ile Trp Pro Phe Gln Tyr Asn Ile Gly Leu
                100                 105                 110

Thr Thr Lys Asp Pro Asn Val Ser Leu Ile Asn Tyr Leu Pro Lys Asn
            115                 120                 125

Lys Ile Glu Thr Thr Asp Val Gly Gln Thr Leu Gly Tyr Asn Ile Gly
        130                 135                 140

Gly Asn Phe Gln Ser Ala Pro Ser Ile Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 9
<211> LENGTH: 311
<212> TYPE: PRT
<213> ORGANISM: Staphylococcus aureus

<400> SEQUENCE: 9

Met Phe Lys Lys Met Leu Ala Ala Thr Leu Ser Val Gly Leu Ile
1               5                  10                  15

Ala Pro Leu Ala Ser Pro Ile Gln Glu Ser Arg Ala Asn Thr Asn Ile
                20                  25                  30

Glu Asn Ile Gly Asp Gly Ala Glu Val Ile Lys Arg Thr Glu Asp Val
            35                  40                  45

Ser Ser Lys Lys Trp Gly Val Thr Gln Asn Val Gln Phe Asp Phe Val
        50                  55                  60

Lys Asp Lys Lys Tyr Asn Lys Asp Ala Leu Ile Val Lys Met Gln Gly
 65                  70                  75                  80

Phe Ile Asn Ser Arg Thr Ser Phe Ser Asp Val Lys Gly Ser Gly Tyr
                 85                  90                  95

Glu Leu Thr Lys Arg Met Ile Trp Pro Phe Gln Tyr Asn Ile Gly Leu
                100                 105                 110

Thr Thr Lys Asp Pro Asn Val Ser Leu Ile Asn Tyr Leu Pro Lys Asn
```

```
            115                 120                 125
Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 10
<211> LENGTH: 311
<212> TYPE: PRT
<213> ORGANISM: Staphylococcus aureus

<400> SEQUENCE: 10

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175
```

```
Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 11
<211> LENGTH: 311
<212> TYPE: PRT
<213> ORGANISM: Staphylococcus aureus

<400> SEQUENCE: 11

Met Phe Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240
```

```
Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
290                 295                 300

Ile Lys Val Lys Gly His Asn
305                 310
```

<210> SEQ ID NO 12
<211> LENGTH: 327
<212> TYPE: PRT
<213> ORGANISM: Staphylococcus aureus

<400> SEQUENCE: 12

```
Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
```

```
                290                 295                 300
Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 13
<211> LENGTH: 327
<212> TYPE: PRT
<213> ORGANISM: Staphylococcus aureus

<400> SEQUENCE: 13

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
                100                 105                 110

Ser Ser Glu Ser Asn Asp Ala Val Asn Val Val Asp Tyr Ala Pro Lys
            115                 120                 125

Asn Gln Asn Glu Glu Phe Gln Val Gln Gln Thr Leu Gly Tyr Ser Tyr
        130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
                180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
        210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
                260                 265                 270

Arg Glu Met Asp Arg Tyr Thr Asn Gln Trp Asn Arg Leu His Trp Val
            275                 280                 285

Gly Asn Asn Tyr Lys Asn Gln Asn Thr Val Thr Phe Thr Ser Thr Tyr
        290                 295                 300

Glu Val Asp Trp Gln Asn His Thr Val Lys Leu Ile Gly Thr Asp Ser
305                 310                 315                 320

Lys Glu Thr Asn Pro Gly Val
                325
```

<210> SEQ ID NO 14
<211> LENGTH: 327
<212> TYPE: PRT
<213> ORGANISM: Staphylococcus aureus

<400> SEQUENCE: 14

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 15
<211> LENGTH: 327
<212> TYPE: PRT
<213> ORGANISM: Staphylococcus aureus

<400> SEQUENCE: 15

```
Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
                100                 105                 110

Ser Ser Glu Ser Asn Asp Ala Val Asn Val Asp Tyr Ala Pro Lys
            115                 120                 125

Asn Gln Asn Glu Glu Phe Gln Val Gln Gln Thr Leu Gly Tyr Ser Tyr
            130                 135                 140

Gly Gly Asp Ile Asn Ile Ser Asn Gly Leu Ser Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
                180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
            210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
            275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 16
<211> LENGTH: 327
<212> TYPE: PRT
<213> ORGANISM: Staphylococcus aureus

<400> SEQUENCE: 16

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45
```

```
Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Asp Thr Leu Val Leu Lys
 65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
               100                 105                 110

Ser Ser Glu Ser Asn Asp Ala Val Asn Val Val Asp Tyr Ala Pro Lys
           115                 120                 125

Asn Gln Asn Glu Glu Phe Gln Val Gln Gln Thr Leu Gly Tyr Ser Tyr
       130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
               165                 170                 175

Thr Thr Ile Asp Arg Lys Thr Asn His Lys Ser Ile Gly Trp Gly Val
               180                 185                 190

Glu Ala His Lys Ile Met Asn Asn Gly Trp Gly Pro Tyr Gly Arg Asp
           195                 200                 205

Ser Tyr Asp Pro Thr Tyr Gly Asn Glu Leu Phe Leu Gly Gly Arg Gln
       210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
               245                 250                 255

His Lys Gln Asn Asp Thr Lys Lys Ser Lys Ile Lys Val Thr Tyr Gln
           260                 265                 270

Arg Glu Met Asp Arg Tyr Thr Asn Gln Trp Asn Arg Leu His Trp Val
       275                 280                 285

Gly Asn Asn Tyr Lys Asn Gln Asn Thr Val Thr Phe Thr Ser Thr Tyr
290                 295                 300

Glu Val Asp Trp Gln Asn His Thr Val Lys Leu Ile Gly Thr Asp Ser
305                 310                 315                 320

Lys Glu Thr Asn Pro Gly Val
               325

<210> SEQ ID NO 17
<211> LENGTH: 327
<212> TYPE: PRT
<213> ORGANISM: Staphylococcus aureus

<400> SEQUENCE: 17

Met Lys Met Lys Lys Leu Val Lys Ser Ser Val Ala Ser Ser Ile Ala
 1               5                  10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Asp Thr Leu Val Leu Lys
 65                  70                  75                  80

Ala Ala Gly Asn Ile Asn Ser Gly Tyr Lys Lys Pro Asn Pro Lys Asp
                85                  90                  95
```

```
                85                  90                  95
Tyr Asn Tyr Ser Gln Phe Tyr Trp Gly Gly Lys Tyr Asn Val Ser Val
            100                 105                 110
Ser Ser Glu Ser Asn Asp Ala Val Asn Val Val Asp Tyr Ala Pro Lys
            115                 120                 125
Asn Gln Asn Glu Glu Phe Gln Val Gln Gln Thr Leu Gly Tyr Ser Tyr
        130                 135                 140
Gly Gly Asp Ile Asn Ile Ser Asn Gly Leu Ser Gly Gly Leu Asn Gly
145                 150                 155                 160
Ser Lys Ser Phe Ser Glu Thr Ile Asn Tyr Lys Gln Glu Ser Tyr Arg
                165                 170                 175
Thr Thr Ile Asp Arg Lys Thr Asn His Lys Ser Ile Gly Trp Gly Val
            180                 185                 190
Glu Ala His Lys Ile Met Asn Asn Gly Trp Gly Pro Tyr Gly Arg Asp
            195                 200                 205
Ser Tyr Asp Pro Thr Tyr Gly Asn Glu Leu Phe Leu Gly Gly Arg Gln
        210                 215                 220
Ser Ser Ser Asn Ala Gly Gln Asn Phe Leu Pro Thr His Gln Met Pro
225                 230                 235                 240
Leu Leu Ala Arg Gly Asn Phe Asn Pro Glu Phe Ile Ser Val Leu Ser
                245                 250                 255
His Lys Gln Asn Asp Thr Lys Lys Ser Lys Ile Lys Val Thr Tyr Gln
            260                 265                 270
Arg Glu Met Asp Arg Tyr Thr Asn Gln Trp Asn Arg Leu His Trp Val
            275                 280                 285
Gly Asn Asn Tyr Lys Asn Gln Asn Thr Val Thr Phe Thr Ser Thr Tyr
        290                 295                 300
Glu Val Asp Trp Gln Asn His Thr Val Lys Leu Ile Gly Thr Asp Ser
305                 310                 315                 320
Lys Glu Thr Asn Pro Gly Val
                325

<210> SEQ ID NO 18
<211> LENGTH: 327
<212> TYPE: PRT
<213> ORGANISM: Staphylococcus aureus

<400> SEQUENCE: 18

Met Lys Met Lys Lys Leu Val Lys Ser Ser Val Ala Ser Ser Ile Ala
1               5                   10                  15
Leu Leu Leu Leu Ser Asn Thr Val Asp Ala Ala Gln His Ile Thr Pro
                20                  25                  30
Val Ser Glu Lys Lys Val Asp Asp Lys Ile Thr Leu Tyr Lys Thr Thr
            35                  40                  45
Ala Thr Ser Asp Asn Asp Lys Leu Asn Ile Ser Gln Ile Leu Thr Phe
        50                  55                  60
Asn Phe Ile Lys Asp Lys Ser Tyr Asp Lys Asp Thr Leu Val Leu Lys
65                  70                  75                  80
Ala Ala Gly Asn Ile Asn Ser Gly Tyr Lys Lys Pro Asn Pro Lys Asp
                85                  90                  95
Tyr Asn Tyr Ser Gln Phe Tyr Trp Gly Gly Lys Tyr Asn Val Ser Val
            100                 105                 110
Ser Ser Glu Ser Asn Asp Ala Val Asn Val Val Asp Tyr Ala Pro Lys
            115                 120                 125
```

```
Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
                180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
                260                 265                 270

Arg Glu Met Asp Arg Tyr Thr Asn Gln Trp Asn Arg Leu His Trp Val
            275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 19
<211> LENGTH: 327
<212> TYPE: PRT
<213> ORGANISM: Staphylococcus aureus

<400> SEQUENCE: 19

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
    115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175
```

```
Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
            210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
            245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
            275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 20
<211> LENGTH: 327
<212> TYPE: PRT
<213> ORGANISM: Staphylococcus aureus

<400> SEQUENCE: 20

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
            85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
            115                 120                 125

Asn Gln Asn Glu Glu Phe Gln Val Gln Gln Thr Leu Gly Tyr Ser Tyr
            130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
            165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
```

```
                210                 215                 220
Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Ser Lys Ile Lys Val Thr Tyr Gln
                260                 265                 270

Arg Glu Met Asp Arg Tyr Thr Asn Gln Trp Asn Arg Leu His Trp Ile
            275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 21
<211> LENGTH: 327
<212> TYPE: PRT
<213> ORGANISM: Staphylococcus aureus

<400> SEQUENCE: 21

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255
```

His Lys Gln Asn Asp Thr Lys Lys Ser Lys Ile Lys Val Thr Tyr Gln
              260                 265                 270

Arg Glu Met Asp Arg Tyr Thr Asn Gln Trp Asn Arg Leu His Trp Ile
          275                 280                 285

Gly Asn Asn Tyr Lys Asn Gln Asn Thr Val Thr Phe Thr Ser Thr Tyr
      290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 22
<211> LENGTH: 327
<212> TYPE: PRT
<213> ORGANISM: Staphylococcus aureus
<220> FEATURE:
<221> NAME/KEY: MISC_FEATURE
<222> LOCATION: (288)..(288)
<223> OTHER INFORMATION: Xaa can be Val or Ile

<400> SEQUENCE: 22

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Xaa

```
            275                 280                 285
Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325
```

LEUKOTOXIN E/D AS A NEW ANTI-INFLAMMATORY AGENT AND MICROBICIDE

This application claims the priority benefit of U.S. Provisional Patent Application Ser. No. 61/498,606, filed Jun. 19, 2011, which is hereby incorporated by reference in its entirety.

FIELD OF THE INVENTION

This invention relates to methods of treating and preventing HIV infections. This invention further relates to method of treating inflammatory conditions and *Staphylococcus aureus* infections.

BACKGROUND OF THE INVENTION

*Staphylococcus aureus*

*Staphylococcus aureus* ("*S. aureus*") is a bacterium that commensally colonizes more than 25% of the human population. Importantly, this organism is capable of breaching its initial site of colonization, resulting in bacterial dissemination and disease. *S. aureus* is the leading cause of nosocomial infections, is the most common etiological agent of infectious endocarditis as well as skin and soft tissue infections, and is one of the four leading causes of food-borne illness. Altogether, *S. aureus* infects more than 1.2 million patients per year in U.S. hospitals. The threat of *S. aureus* to human health is further highlighted by the emergence of antibiotic-resistant strains (i.e., methicillin-resistant *S. aureus* (MRSA) strains), including strains that are resistant to vancomycin, an antibiotic considered the last line of defense against *S. aureus* infection. These facts highlight the importance of developing novel therapeutics against this important pathogen.

*S. aureus* produces a diverse array of virulence factors and toxins that enable this bacterium to neutralize and withstand attack by different kinds of immune cells, specifically subpopulations of white blood cells that make up the body's primary defense system. The production of these virulence factors and toxins allow *S. aureus* to maintain an infectious state (Nizet, "Understanding How Leading Bacterial Pathogens Subvert Innate Immunity to Reveal Novel Therapeutic Targets," *J. Allergy Clin. Immunol.* 120(1):13 22 (2007)). Among these virulence factors, *S. aureus* produces several bi-component leukotoxins, which damage membranes of host defense cells and erythrocytes by the synergistic action of two non-associated proteins or subunits (see Menestrina et al., "Mode of Action of Beta-Barrel Pore-Forming Toxins of the Staphylococcal Alpha-Hemolysin Family," *Toxicol.* 39(11):1661-1672 (2001)). Among these bi-component leukotoxins, gamma-hemolysin (HlgAB and HlgCB) and the Pantone-Valentine Leukocidin (PVL) are the best characterized.

The toxicity of the leukocidins towards mammalian cells involves the action of two components. The first subunit is named class S-subunit (i.e., "slow-eluted"), and the second subunit is named class F-subunit (i.e., "fast-eluted"). The S- and F-subunits act synergistically to form pores on white blood cells including monocytes, macrophages, dendritic cells and neutrophils (collectively known as phagocytes) (Menestrina et al., "Mode of Action of Beta-Barrel Pore-Forming Toxins of the Staphylococcal Alpha-Hemolysin Family," *Toxicol.* 39(11):1661 1672 (2001)). The mechanism by which the bi-component toxins form pores in target cell membranes is not entirely understood. The proposed mechanism of action of these toxins involves binding of the S-subunit to the target cell membrane, most likely through a receptor, followed by binding of the F-subunit to the S-subunit, thereby forming an oligomer which in turn forms a pre-pore that inserts into the target cell membrane (Jayasinghe et al., "The Leukocidin Pore Evidence for an Octamer With Four LukF Subunits and Four LukS Subunits Alternating Around a Central Axis," *Protein. Sci.* 14(10):2550 2561 (2005)). The pores formed by the bi-component leukotoxins are typically cation-selective. Pore formation causes cell death via lysis, which in the cases of the target white blood cells, has been reported to result from an osmotic imbalance due to the influx of cations (Miles et al., "The Staphylococcal Leukocidin Bicomponent Toxin Forms Large Ionic Channels," *Biochemistry* 40(29):8514 8522 (2001)).

Designing effective therapy to treat MRSA infection has been especially challenging. In addition to the resistance to methicillin and related antibiotics, MRSA has also been found to have significant levels of resistance to macrolides (e.g., erythromycin), beta-lactamase inhibitor combinations (e.g., Unasyn, Augmentin) and fluoroquinolones (e.g. ciprofloxacin), as well as to clindamycin, trimethoprim/sulfamethoxisol (Bactrim), and rifampin. In the case of serious *S. aureus* infection, clinicians have resorted to intravenous vancomycin. However, there have been reports of *S. aureus* resistance to vancomycin. Thus, there is a need to develop new antibiotic drugs that effectively combat *S. aureus* infection.

C—C Chemokine Receptor Type 5

C—C chemokine receptor type 5 (CCR5) is a member of the beta chemokine receptors family (Samson M et al., "Molecular Cloning and Functional Expression of a New Human CC-Chemokine Receptor Gene" *Biochemistry* 35:3362 (1996)). The normal ligands for this receptor are RANTES, Mip1b, and Mip1a (see Samson, supra and Gon W et al "Monocyte Chemotactic Protein-2 Activates CCR5 and Blocks CD4/CCR5 Mediated HIV-1 Entry/Replication," *J. Biol. Chem.* 273:4289 (1998)). CCR5 is expressed on a subset of T cells, macrophages, dendritic cells, natural killer cells, and microglia. $CCR5^+$ T cells secrete pro-inflammatory cytokines and are recruited to sites of inflammation. Thus, it is likely that CCR5 plays a role in inflammatory responses to infection and in pathological conditions such as autoimmune diseases. CCR5 is also the receptor for major strain of HIV (Deng H et al., "Identification of a Major Co-Receptor for Primary Isolates of HIV-1," *Nature* 381:661-666 (1996)). In individuals infected with HIV, CCR5-using viruses are the predominant species isolated during the early stages of viral infection, suggesting that these viruses may have a selective advantage during transmission or the acute phase of disease. Moreover, at least half of all infected individuals harbor only CCR5-using viruses throughout the course of infection. Around 1% of Northern Europeans lack functional CCR5 expression, due to a 32 base pair deletion in this gene. Individuals with the Δ32 allele of CCR5 are healthy, suggesting that CCR5 is largely dispensable. However, these individuals have very strong resistance to HIV infection (Liu R et al., "Homozygous Defect in HIV-1 Coreceptor Accounts for Resistance of Some Multiply-Exposed Individuals to HIV-1 Infection," *Cell* 86:367-377 (1996)). Indeed, an AIDS patient who had myeloid leukemia was treated with chemotherapy to suppress the cancer, which killed all of his T cells. The patient was then transplanted with a donor blood that had the 32 bp CCR5 deletion mutant to restore the immune system. After 600 days, the patient was healthy and had undetectable levels of HIV in the blood and in examined brain and rectal tissues (Witter G et al., "Long-Term Control of HIV by CCR5 Delta32/Delta32 Stem-Cell Transplantation," *N. Engl. J.*

Med. 360:692-698 (2009)). A number of new experimental HIV drugs, called entry inhibitors have been designed to interfere with the interaction between CCR5 and HIV, including PRO140, Vicriviroc, Aploviroc, and Maraviroc (Pfizer), of which the latter is currently an approved drug for HIV infection.

CCR5 is also involved in uncontrolled inflammation (Charo et al., "The Many Roles of Chemokine Receptors in Inflammation," N. Engl. J. Med. 354:610-621 (2006)). This association is based on the role of this chemokine receptor in the recruitment of inflammatory leukocytes. In particular, CCR5 is expressed in a subset of effector T cells that produce proinflammatory cytokines such as interferon gamma (IFNg) and interleukin-17 (IL-17), which are enriched locally during inflammation. Thus, CCR5 is being considered as a target to dampen inflammatory disorders, such as rheumatoid arthritis (RA), Crohn's Disease (CD), atherosclerosis, and psoriasis among others.

The present invention is directed to overcoming these and other limitations in the art.

SUMMARY OF THE INVENTION

A first aspect of the present invention relates to a method of preventing or treating Human Immunodeficiency Virus (HIV) infection in a subject. This method involves administering a composition comprising an isolated Leukocidin E (LukE) protein, or polypeptide thereof, and an isolated Leukocidin D (LukD) protein, or polypeptide thereof in an amount effective to prevent or treat HIV infection in the subject.

Another aspect of the present invention relates to a method of preventing HIV infection in a subject. This method involves providing a composition comprising an isolated LukE protein, or polypeptide thereof, and an isolated LukD protein, or polypeptide thereof, and contacting the tissue of the subject with the composition under conditions effective to block HIV infectivity of cells in the tissue, thereby inhibiting HIV infection of the subject.

Another aspect of the present invention relates to a composition comprising a therapeutically effective amount of an isolated LukE protein or polypeptide thereof, an isolated LukD protein or polypeptide thereof, or a combination thereof, and one or more additional agents selected from the group consisting of a lubricant, an antimicrobial agent, a humectant, an emulsifier, and a mixture of two or more thereof.

Another aspect of the invention relates to a method of treating an inflammatory condition in a subject. This method involves administering a composition comprising an isolated LukE protein, or polypeptide thereof, and an isolated LukD protein, or polypeptide thereof, in an amount effective to treat an inflammatory condition in the subject.

Another aspect of the present invention relates to a method of preventing graft-versus-host-disease (GVHD) in a subject. This method involves administering a composition comprising an isolated LukE protein, or polypeptide thereof, and an isolated LukD protein, or polypeptide thereof, in an amount effective to prevent graft-versus-host-disease (GVHD) in the subject.

Another aspect of the present invention relates to a method of treating a Staphylococcus aureus infection in a subject. This method involves selecting a subjecting having a S. aureus infection and administering a composition comprising a CCR5 antagonist to the subject in an amount effective to treat the S. aureus infection in the subject.

As demonstrated herein, applicants have found that the bi-component leukotoxin of Staphylococcus aureus, leukocidin E/D, mediates its cytotoxicity via the CCR5 receptor on the surface of leukocytes. Exploitation of this toxin-receptor interaction has a number of therapeutic implications. Firstly, since LukE/D significantly contributes to the pathogenesis of S. aureus infections, CCR5 receptor antagonists offer a novel therapeutic approach to treat S. aureus infections, especially infections caused by MRSA strains. Secondly, due to its role in mediating HIV infectivity, a variety of CCR5 antagonists are being tested in clinical trials as anti-HIV drugs. Use of composition containing LukE and LukD to target latently infected cells in HIV-infected individuals represents a superior therapeutic strategy compared to CCR5-antagonism, because use of this toxin will deplete all CCR5 positive cells, thereby eliminating HIV positive cells. A composition containing LukE and LukD can also be administered prophylactically to prevent the transmission of HIV by killing CCR5-positive cells that are required for HIV transmission. These therapeutic approaches are novel because they will eradicate HIV cells or cells susceptible to HIV infection in a subject. Finally, since CCR5 is also involved in uncontrolled inflammation, use of a LukE/D composition to target and deplete CCR5 positive cells offers a new treatment modality to combat localized inflammatory conditions. This treatment approach is highly targeted to the source of inflammation, thereby avoiding side effects often encountered with current anti-inflammatory strategies.

BRIEF DESCRIPTION OF THE DRAWINGS

FIG. 1A demonstrates that LukE/D is critical for the death of mice infected systemically with S. aureus. The survival of mice was monitored after intravenous injection with ~1×10$^7$ CFU with S. aureus strain Newman wild type, a ΔlukE/D mutant, and the complemented ΔlukE/D::plukE/D strain. Total number of mice per group were N=6. Statistical significance between survival curves was determined using the Log-rank (Mantel-Cox) test (p≤0.0005). FIG. 1B demonstrates that LukE/D is required for S. aureus proliferation in vivo. The bacterial burden was determined by enumeration of bacterial CFU from kidneys 96 hours post-infection as described for FIG. 1A. Statistical significance was determined using 1-Way ANOVA with Tukey's multiple comparisons posttest (***, p≤0.0005).

FIG. 2A demonstrates that LukE/D is selectively toxic to the monocyte-like cell line THP-1 and the T lymphocyte-like cell line Hut cells. Cytotoxicity was determined by a cell viability assay where indicated human immune cells lines were intoxicated with different concentrations of an equimolar mixture of LukE+LukD (LukE/D). Cell viability was monitored 1 hour post-intoxication using CellTiter, where cells treated with medium were set at 100% viable. Results represent the average of triplicate samples ±S.D. FIG. 2B depicts that LukE/D kills Hut cell but not other human T lymphocyte-like cell lines. Indicated cell lines were intoxicated with different concentrations of an equimolar mixture of LukE+LukD (LukE/D) and cell viability monitored as in FIG. 2A. Results represent the average of triplicate samples ±S.D.

FIG. 4A demonstrates that CCR5-specific antagonist potently block LukE/D cytotoxicity towards CCR5+ cells. CCR5+ Jurkats were preincubated with different concentrations of Maraviroc (MVC), Vicriviroc (VVC), or TAK-779 (TAK) for 30 minutes followed by intoxication with an equimolar mixture of LukE+LukD (LukE/D). One hour post-intoxication, the percent death was determined by CellTiter where cells treated with media+LukE/D was set to 100% cell death. Results represent the average of triplicate samples ±S.D. FIG. 4B demonstrates that monoclonal antibodies directed towards CCR5 inhibit LukE/D cytotoxicity towards CCR5+ cells. CCR5+ Jurkats were preincubated with indicated monoclonal antibodies for 30 minutes followed by intoxication with an equimolar mixture of LukE+LukD (LukE/D). One hour post-intoxication, the viability of the cells was determined by CellTiter. Results represent the average of triplicate samples ±S.D. FIG. 4C demonstrates that CCR5 ligands inhibit LukE/D cytotoxicity towards CCR5+ cells. CCR5+ Jurkats were preincubated with buffer (PBS; negative control) or different concentrations of the indicated ligands for 30 minutes followed by intoxication with an equimolar mixture of LukE+LukD (LukE/D). One hour post-intoxication, the viability of the cells was determined by CellTiter. Results represent the average of triplicate samples ±S.D.

FIG. 5A demonstrates that LukE/D binds to host cells in a CCR5-dependent manner and that this binding is potently inhibited by Maraviroc. Jurkat (CCR5−) and CCR5+ Jurkat (CCR5+) cells were preincubated with buffer or with Maraviroc (CCR5++MVC) followed by incubation of an equimoler mixture of a green fluorescent protein (GFP) fused LukE with LukD toxin ($^{GFP}$LukE/D). Binding of the toxin to the plasma membrane of the cells was monitored via flow cytometry. FIG. 5B demonstrates that LukE/D forms pores in the plasma membrane of CCR5+ cells, which are potently blocked by Maraviroc. CCR5+ Jurkat cells were pre-incubated with Maraviroc (MVC) and subsequently intoxicated with an equimolar mixture of LukE+LukD (LukE/D) in the presence of ethidium bromide. Pore formation was measured over-time by monitoring ethidium bromide incorporation. Results represent the average of triplicate samples ±S.D. FIG. 5C show that pore formation by LukE/D is associated with cell swelling, a cytophatic effect potently inhibited by Maraviroc. CCR5+ Jurkat cells were pre-incubated with buffer (NO MVC) or with Maraviroc (MVC) and subsequently intoxicated with an equimolar mixture of LukE+LukD (LukE/D) in the presence of ethidium bromide. Intoxicated cells were monitored by light (top panels) and by fluorescence microscopy to determine ethidium bromide uptake. Representative images are shown.

FIG. 6A demonstrates that LukE/D targets primary human T lymphocytes in a CCR5-dependent manner. T cells from human peripheral blood mononuclear cells (PBMC) from wild type CCR5 and a Δ32CCR5 donor were expanded in vitro and subsequently incubated with media (negative control), an equimolar mixture of LukE+LukD (LukE/D), or with Maraviroc (MVC) followed by intoxication with an equimolar mixture of LukE+LukD (LukE/D). Cells were then stained with an anti-CCR5 antibody and a viability dye prior analysis by flow cytometry. FIGS. 6B-6C demonstrate that LukE/D is cytotoxic towards primary human macrophages (FIG. 6B) and primary human dendtric cells (FIG. 6C) and that Maraviroc potently protects these cells from LukE/D mediated cytotoxicity. Macrophages and dendritic cells were incubated with media (negative control), an equimolar mixture of LukE+LukD (LukE/D), or with Maraviroc (MVC) followed by intoxication with an equimolar mixture of LukE+LukD (LukE/D). One hour post-intoxication, the percent death was determined by flow cytometry.

DETAILED DESCRIPTION OF THE INVENTION

Figures 1A, 1B:
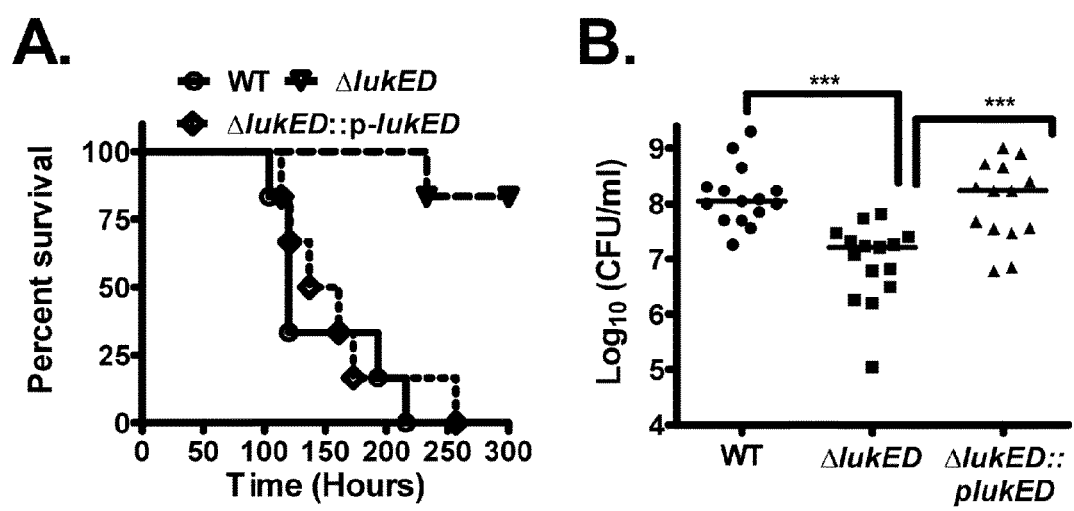
FIGS. 1A-1B illustrate that LukE/D contributes to S. aureus infection in a mouse model of systemic infection.

A first aspect of the present invention relates to a composition comprising a therapeutically effective amount of an isolated LukE protein or polypeptide thereof, an isolated LukD protein or polypeptide thereof, and a pharmaceutically acceptable carrier.

In accordance with this aspect of the invention, suitable isolated LukE proteins include those derived from any strain of S. aureus. The amino acid sequence of LukE proteins from various strains of S. aureus that are suitable for the composition of the present invention are shown in the Table 1 below (i.e., SEQ ID Nos: 1-10). SEQ ID NO: 11 of Table 1 is a LukE consensus sequence demonstrating the high level of sequence identity across LukE proteins of various S. aureus strains. Accordingly, in one embodiment of the present invention, the isolated LukE protein comprises an amino acid sequence of SEQ ID NO:11. In another embodiment of the present invention, the isolated LukE protein comprises an amino acid sequence having about 70-80% sequence similarity to SEQ ID NO:11, more preferably, about 80-90% sequence similarity to SEQ ID NO:11, and more preferably 90-95% sequence similarity to SEQ ID NO:11, and most preferably about 95-99% sequence similarity to SEQ ID NO:11.

In another embodiment of the present invention, the composition comprises an isolated polypeptide of LukE Suitable LukE polypeptides are about 50 to about 100 amino acids in length. More preferably LukE polypeptides are between about 100-200 amino acids in length, more preferably between about 200-250 amino acids in length, and most preferably between 250-300 amino acids in length. The N-terminal amino acid residues of the full-length LukE represent the native secretion/signal sequence. Thus, the "mature" secreted form of LukE is represented by amino acid residues 29-311 in each of SEQ ID NOs: 1-10 and SEQ ID NO:11. Correspondingly, amino acid residues 1-311 in each of SEQ ID NOs: 1-10 and SEQ ID NO:11 are referred to as the "immature" form of LukE Accordingly, in one embodiment of the present invention, the LukE polypeptide comprises amino acid residues 29-311 of SEQ ID NO:11., amino acid residues 48-291 of SEQ ID NO:11, amino acid residues 29-301 of SEQ ID NO:11, and amino acids 48-301 of SEQ ID NO:11. In either case, suitable LukE polypeptides also include those polypeptides comprising an amino acid sequence having about 70-80% sequence similarity, preferably 80-90% sequence similarity, more preferably 90-95% sequence similarity, and most preferably 95-99% sequence similarity to amino acid residues 29-311 of SEQ ID NO:11 or 48-291 of SEQ ID NO: 11.

In accordance with this aspect of the invention, suitable isolated LukD proteins include those proteins derived from any strain of S. aureus. The amino acid sequence of LukD proteins from various strains of S. aureus that are suitable for the composition of the present invention are shown in the Table 2 below (i.e., SEQ ID Nos: 12-21). SEQ ID NO: 22 of Table 2 is a LukD consensus sequence demonstrating the high level of sequence identity across LukD proteins of various *S. aureus* strains. Accordingly, in one embodiment of the present invention, the isolated LukD protein comprises an amino acid sequence of SEQ ID NO:22. In another embodiment of the present invention, the isolated LukD protein comprises an amino acid sequence having about 70-80% sequence similarity to SEQ ID NO:22, preferably, about 80-90% sequence similarity to SEQ ID NO:22, and more preferably 90-95% sequence similarity to SEQ ID NO:22, and most preferably about 95-99% sequence similarity to SEQ ID NO:22.

In another embodiment of the present invention, the composition comprises an isolated polypeptide of LukD. Suitable LukD polypeptides are about 50 to about 100 amino acids in length. More preferably LukD polypeptides are between about 100-200 amino acids in length, more preferably between about 200-250 amino acids in length, and most preferably between 250-300 amino acids in length. The N-terminal amino acid residues of the full length LukD represent the native secretion/signal sequence. Thus, the mature secreted form of LukD is represented by amino acid residues 27-327 in each of SEQ ID NOs: 12-21 and SEQ ID NO: 22. Correspondingly, amino acid residues 1-327 of SEQ ID NOs: 12-21 and SEQ ID NO: 22 are referred to as the "immature" form of LukD. Accordingly, in one embodiment of the present invention, the LukD polypeptide comprises amino acid residues 27-327 of SEQ ID NO:22. Alternatively, the LukD polypeptide of the present invention comprises amino acid residues 46-307, amino acid residues 27-312, and amino acid residues 46-312 of SEQ ID NO:22. In either case, suitable polypeptides also include those polypeptide comprising an amino acid sequence having about 70-80% sequence similarity, preferably 80-90% sequence similarity, more preferably 90-95% sequence similarity, and most preferably 95-99% sequence similarity to amino acid residues 27-327 of SEQ ID NO:22, amino acid residues of 46-307 of SEQ ID NO:22, amino acid residues of 46-312 of SEQ ID NO:22, or amino acid residues of 27-312 of SEQ ID NO:22.

TABLE 1

*S. Aureus* LukE Sequence Alignment

| *S. Aureus* Strain | | | |
|---|---|---|---|
| Newman | MFKKKMLAATLSVGLIAPLASPIQESRANTNIENIGDGAEVIKRTEDVSS | 50 | SEQ ID NO: 1 |
| MW2 | MFKKKMLAATLSVGLIAPLASPIQESRANTNIENIGDGAEVIKRTEDVSS | 50 | SEQ ID NO: 2 |
| USA_300_FPR3757 | MFKKKMLAATLSVGLIAPLASPIQESRANTNIENIGDGAEVIKRTEDVSS | 50 | SEQ ID NO: 3 |
| COL | MFKKKMLAATLSVGLIAPLASPIQESRANTNIENIGDGAEVIKRTEDVSS | 50 | SEQ ID NO: 4 |
| USA_300_TCH1516 | MFKKKMLAATLSVGLIAPLASPIQESRANTNIENIGDGAEVIKRTEDVSS | 50 | SEQ ID NO: 5 |
| N315 | MFKKKMLAATLSVGLIAPLASPIQESRANTNIENIGDGAEVIKRTEDVSS | 50 | SEQ ID NO: 6 |
| D30 | MFKKKMLAATLSVGLIAPLASPIQESRANTNIENIGDGAEVIKRTEDVSS | 50 | SEQ ID NO: 7 |
| Mu50 | MFKKKMLAATLSVGLIAPLASPIQESRANTNIENIGDGAEVIKRTEDVSS | 50 | SEQ ID NO: 8 |
| TCH_70 | MFKKKMLAATLSVGLIAPLASPIQESRANTNIENIGDGAEVIKRTEDVSS | 50 | SEQ ID NO: 9 |
| MRSA131 | MFKKKMLAATLSVGLIAPLASPIQESRANTNIENIGDGAEVIKRTEDVSS | 50 | SEQ ID NO: 10 |
| | ************************************************** | | |
| LukE Consensus Sequence | MFKKKMLAATLSVGLIAPLASPIQESRANTNIENIGDGAEVIKRTEDVSS | 50 | SEQ ID NO: 11 |
| Newman | KKWGVTQNVQFDFVKDKKYNKDALIVKMQGFINSRTSFSDVKGSGYELTK | 100 | |
| MW2 | KKWGVTQNVQFDFVKDKKYNKDALIVKMQGFINSRTSFSDVKGSGYELTK | 100 | |
| USA_300_FPR3757 | KKWGVTQNVQFDFVKDKKYNKDALIVKMQGFINSRTSFSDVKGSGYELTK | 100 | |
| COL | KKWGVTQNVQFDFVKDKKYNKDALIVKMQGFINSRTSFSDVKGSGYELTK | 100 | |
| USA_300_TCH1516 | KKWGVTQNVQFDFVKDKKYNKDALIVKMQGFINSRTSFSDVKGSGYELTK | 100 | |
| N315 | KKWGVTQNVQFDFVKDKKYNKDALIVKMQGFINSRTSFSDVKGSGYELTK | 100 | |
| D30 | KKWGVTQNVQFDFVKDKKYNKDALIVKMQGFINSRTSFSDVKGSGYELTK | 100 | |
| Mu50 | KKWGVTQNVQFDFVKDKKYNKDALIVKMQGFINSRTSFSDVKGSGYELTK | 100 | |
| TCH_70 | KKWGVTQNVQFDFVKDKKYNKDALIVKMQGFINSRTSFSDVKGSGYELTK | 100 | |
| MRSA131 | KKWGVTQNVQFDFVKDKKYNKDALIVKMQGFINSRTSFSDVKGSGYELTK | 100 | |
| | ************************************************** | | |
| LukE Consensus Sequence | KKWGVTQNVQFDFVKDKKYNKDALIVKMQGFINSRTSFSDVKGSGYELTK | | |
| Newman | RMIWPFQYNIGLTTKDPNVSLINYLPKNKIETTDVGQTLGYNIGGNFQSA | 150 | |
| MW2 | RMIWPFQYNIGLTTKDPNVSLINYLPKNKIETTDVGQTLGYNIGGNFQSA | 150 | |
| USA_300_FPR3757 | RMIWPFQYNIGLTTKDPNVSLINYLPKNKIETTDVGQTLGYNIGGNFQSA | 150 | |
| COL | RMIWPFQYNIGLTTKDPNVSLINYLPKNKIETTDVGQTLGYNIGGNFQSA | 150 | |
| USA_300_TCH1516 | RMIWPFQYNIGLTTKDPNVSLINYLPKNKIETTDVGQTLGYNIGGNFQSA | 150 | |
| N315 | RMIWPFQYNIGLTTKDPNVSLINYLPKNKIETTDVGQTLGYNIGGNFQSA | 150 | |
| D30 | RMIWPFQYNIGLTTKDPNVSLINYLPKNKIETTDVGQTLGYNIGGNFQSA | 150 | |
| Mu50 | RMIWPFQYNIGLTTKDPNVSLINYLPKNKIETTDVGQTLGYNIGGNFQSA | 150 | |
| TCH_70 | RMIWPFQYNIGLTTKDPNVSLINYLPKNKIETTDVGQTLGYNIGGNFQSA | 150 | |
| MRSA131 | RMIWPFQYNIGLTTKDPNVSLINYLPKNKIETTDVGQTLGYNIGGNFQSA | 150 | |
| | ************************************************** | | |
| LukE Consensus Sequence | RMIWPFQYNIGLTTKDPNVSLINYLPKNKIETTDVGQTLGYNIGGNFQSA | | |
| Newman | PSIGGNGSFNYSKTISYTQKSYVSEVDKQNSKSVKWGVKANEFVTPDGKK | 200 | |
| MW2 | PSIGGNGSFNYSKTISYTQKSYVSEVDKQNSKSVKWGVKANEFVTPDGKK | 200 | |
| USA_300_FPR3757 | PSIGGNGSFNYSKTISYTQKSYVSEVDKQNSKSVKWGVKANEFVTPDGKK | 200 | |
| COL | PSIGGNGSFNYSKTISYTQKSYVSEVDKQNSKSVKWGVKANEFVTPDGKK | 200 | |
| USA_300_TCH1516 | PSIGGNGSFNYSKTISYTQKSYVSEVDKQNSKSVKWGVKANEFVTPDGKK | 200 | |
| N315 | PSIGGNGSFNYSKTISYTQKSYVSEVDKQNSKSVKWGVKANEFVTPDGKK | 200 | |
| D30 | PSIGGNGSFNYSKTISYTQKSYVSEVDKQNSKSVKWGVKANEFVTPDGKK | 200 | |
| Mu50 | PSIGGNGSFNYSKTISYTQKSYVSEVDKQNSKSVKWGVKANEFVTPDGKK | 200 | |

TABLE 1-continued

S. Aureus LukE Sequence Alignment

| | | |
|---|---|---|
| TCH_70 | PSIGGNGSFNYSKTISYTQKSYVSEVDKQNSKSVKWGVKANEFVTPDGKK | 200 |
| MRSA131 | PSIGGNGSFNYSKTISYTQKSYVSEVDKQNSKSVKWGVKANEFVTPDGKK | 200 |
| | ************************************************** | |
| | | |
| LukE Consensus Sequence | PSIGGNGSFNYSKTISYTQKSYVSEVDKQNSKSVKWGVKANEFVTPDGKK | |
| | | |
| Newman | SAHDRYLFVQSPNGPTGSAREYFAPDNQLPPLVQSGFNPSFITTLSHEKG | 250 |
| MW2 | SAHDRYLFVQSPNGPTGSAREYFAPDNQLPPLVQSGFNPSFITTLSHEKG | 250 |
| USA_300_FPR3757 | SAHDRYLFVQSPNGPTGSAREYFAPDNQLPPLVQSGFNPSFITTLSHEKG | 250 |
| COL | SAHDRYLFVQSPNGPTGSAREYFAPDNQLPPLVQSGFNPSFITTLSHEKG | 250 |
| USA_300_TCH1516 | SAHDRYLFVQSPNGPTGSAREYFAPDNQLPPLVQSGFNPSFITTLSHEKG | 250 |
| N315 | SAHDRYLFVQSPNGPTGSAREYFAPDNQLPPLVQSGFNPSFITTLSHEKG | 250 |
| D30 | SAHDRYLFVQSPNGPTGSAREYFAPDNQLPPLVQSGFNPSFITTLSHEKG | 250 |
| Mu50 | SAHDRYLFVQSPNGPTGSAREYFAPDNQLPPLVQSGFNPSFITTLSHEKG | 250 |
| TCH_70 | SAHDRYLFVQSPNGPTGSAREYFAPDNQLPPLVQSGFNPSFITTLSHEKG | 250 |
| MRSA131 | SAHDRYLFVQSPNGPTGSAREYFAPDNQLPPLVQSGFNPSFITTLSHEKG | 250 |
| | ************************************************** | |
| | | |
| LukE Consensus Sequence | SAHDRYLFVQSPNGPTGSAREYFAPDNQLPPLVQSGFNPSFITTLSHEKG | |
| | | |
| Newman | SSDTSEFEISYGRNLDITYATLFPRTGIYAERKHNAFVNRNFVVRYEVNW | 300 |
| MW2 | SSDTSEFEISYGRNLDITYATLFPRTGIYAERKHNAFVNRNFVVRYEVNW | 300 |
| USA_300_FPR3757 | SSDTSEFEISYGRNLDITYATLFPRTGIYAERKHNAFVNRNFVVRYEVNW | 300 |
| COL | SSDTSEFEISYGRNLDITYATLFPRTGIYAERKHNAFVNRNFVVRYEVNW | 300 |
| USA_300_TCH1516 | SSDTSEFEISYGRNLDITYATLFPRTGIYAERKHNAFVNRNFVVRYEVNW | 300 |
| N315 | SSDTSEFEISYGRNLDITYATLFPRTGIYAERKHNAFVNRNFVVRYEVNW | 300 |
| D30 | SSDTSEFEISYGRNLDITYATLFPRTGIYAERKHNAFVNRNFVVRYEVNW | 300 |
| Mu50 | SSDTSEFEISYGRNLDITYATLFPRTGIYAERKHNAFVNRNFVVRYEVNW | 300 |
| TCH_70 | SSDTSEFEISYGRNLDITYATLFPRTGIYAERKHNAFVNRNFVVRYEVNW | 300 |
| MRSA131 | SSDTSEFEISYGRNLDITYATLFPRTGIYAERKHNAFVNRNFVVRYEVNW | 300 |
| | ************************************************** | |
| | | |
| LukE Consensus Sequence | SSDTSEFEISYGRNLDITYATLFPRTGIYAERKHNAFVNRNFVVRYEVNW | |
| | | |
| Newman | KTHEIKVKGHN | 311 |
| MW2 | KTHEIKVKGHN | 311 |
| USA_300_FPR3757 | KTHEIKVKGHN | 311 |
| COL | KTHEIKVKGHN | 311 |
| USA_300_TCH1516 | KTHEIKVKGHN | 311 |
| N315 | KTHEIKVKGHN | 311 |
| D30 | KTHEIKVKGHN | 311 |
| Mu50 | KTHEIKVKGHN | 311 |
| TCH_70 | KTHEIKVKGHN | 311 |
| MRSA131 | KTHEIKVKGHN | 311 |
| | *********** | |
| | | |
| LukE Consensus Sequence | KTHEIKVKGHN | |

→ Depicts the start of the secreted LukE protein

TABLE 2

LukD Amino Acid Sequence Alignment

| | → | | |
|---|---|---|---|
| Newman | MKMKKLVKSSVASSIALLLLSNTVDAAQHITPVSEKKVDDKITLYKTTAT | 50 | SEQ ID NO: 12 |
| MW2 | MKMKKLVKSSVASSIALLLLSNTVDAAQHITPVSEKKVDDKITLYKTTAT | 50 | SEQ ID NO: 13 |
| USA_300_FPR3757 | MKMKKLVKSSVASSIALLLLSNTVDAAQHITPVSEKKVDDKITLYKTTAT | 50 | SEQ ID NO: 14 |
| COL | MKMKKLVKSSVASSIALLLLSNTVDAAQHITPVSEKKVDDKITLYKTTAT | 50 | SEQ ID NO: 15 |
| USA_300_TCH1516 | MKMKKLVKSSVASSIALLLLSNTVDAAQHITPVSEKKVDDKITLYKTTAT | 50 | SEQ ID NO: 16 |
| MRSA131 | MKMKKLVKSSVASSIALLLLSNTVDAAQHITPVSEKKVDDKITLYKTTAT | 50 | SEQ ID NO: 17 |
| TCH_70 | MKMKKLVKSSVASSIALLLLSNTVDAAQHITPVSEKKVDDKITLYKTTAT | 50 | SEQ ID NO: 18 |
| D30 | MKMKKLVKSSVASSIALLLLSNTVDAAQHITPVSEKKVDDKITLYKTTAT | 50 | SEQ ID NO: 19 |
| N315 | MKMKKLVKSSVASSIALLLLSNTVDAAQHITPVSEKKVDDKITLYKTTAT | 50 | SEQ ID NO: 20 |
| Mu50 | MKMKKLVKSSVASSIALLLLSNTVDAAQHITPVSEKKVDDKITLYKTTAT | 50 | SEQ ID NO: 21 |
| | ************************************************** | | |
| | | | |
| LukD Consensus Sequence | MKMKKLVKSSVASSIALLLLSNTVDAAQHITPVSEKKVDDKITLYKTTAT | 50 | SEQ ID NO: 22 |
| | | | |
| Newman | SDNDKLNISQILTFNFIKDKSYDKDTLVLKAAGNINSGYKKPNPKDYNYS | 100 | |
| MW2 | SDNDKLNISQILTFNFIKDKSYDKDTLVLKAAGNINSGYKKPNPKDYNYS | 100 | |
| USA_300_FPR3757 | SDNDKLNISQILTFNFIKDKSYDKDTLVLKAAGNINSGYKKPNPKDYNYS | 100 | |
| COL | SDNDKLNISQILTFNFIKDKSYDKDTLVLKAAGNINSGYKKPNPKDYNYS | 100 | |
| USA_300_TCH1516 | SDNDKLNISQILTFNFIKDKSYDKDTLVLKAAGNINSGYKKPNPKDYNYS | 100 | |
| MRSA131 | SDNDKLNISQILTFNFIKDKSYDKDTLVLKAAGNINSGYKKPNPKDYNYS | 100 | |
| TCH_70 | SDNDKLNISQILTFNFIKDKSYDKDTLVLKAAGNINSGYKKPNPKDYNYS | 100 | |

TABLE 2-continued

LukD Amino Acid Sequence Alignment

```
D30                  SDNDKLNISQILTFNFIKDKSYDKDTLVLKAAGNINSGYKKPNPKDYNYS 100
N315                 SDNDKLNISQILTFNFIKDKSYDKDTLVLKAAGNINSGYKKPNPKDYNYS 100
Mu50                 SDNDKLNISQILTFNFIKDKSYDKDTLVLKAAGNINSGYKKPNPKDYNYS 100
                     **************************************************

LukD Consensus Sequence SDNDKLNISQILTFNFIKDKSYDKDTLVLKAAGNINSGYKKPNPKDYNYS

Newman               QFYWGGKYNVSVSSESNDAVNVVDYAPKNQNEEFQVQQTLGYSYGGDINI 150
MW2                  QFYWGGKYNVSVSSESNDAVNVVDYAPKNQNEEFQVQQTLGYSYGGDINI 150
USA_300_FPR3757      QFYWGGKYNVSVSSESNDAVNVVDYAPKNQNEEFQVQQTLGYSYGGDINI 150
COL                  QFYWGGKYNVSVSSESNDAVNVVDYAPKNQNEEFQVQQTLGYSYGGDINI 150
USA_300_TCH1516      QFYWGGKYNVSVSSESNDAVNVVDYAPKNQNEEFQVQQTLGYSYGGDINI 150
MRSA131              QFYWGGKYNVSVSSESNDAVNVVDYAPKNQNEEFQVQQTLGYSYGGDINI 150
TCH_70               QFYWGGKYNVSVSSESNDAVNVVDYAPKNQNEEFQVQQTLGYSYGGDINI 150
D30                  QFYWGGKYNVSVSSESNDAVNVVDYAPKNQNEEFQVQQTLGYSYGGDINI 150
N315                 QFYWGGKYNVSVSSESNDAVNVVDYAPKNQNEEFQVQQTLGYSYGGDINI 150
Mu50                 QFYWGGKYNVSVSSESNDAVNVVDYAPKNQNEEFQVQQTLGYSYGGDINI 150
                     **************************************************

LukD Consensus Sequence QFYWGGKYNVSVSSESNDAVNVVDYAPKNQNEEFQVQQTLGYSYGGDINI

Newman               SNGLSGGLNGSKSFSETINYKQESYRTTIDRKTNHKSIGWGVEAHKIMNN 200
MW2                  SNGLSGGLNGSKSFSETINYKQESYRTTIDRKTNHKSIGWGVEAHKIMNN 200
USA_300_FPR3757      SNGLSGGLNGSKSFSETINYKQESYRTTIDRKTNHKSIGWGVEAHKIMNN 200
COL                  SNGLSGGLNGSKSFSETINYKQESYRTTIDRKTNHKSIGWGVEAHKIMNN 200
USA_300_TCH1516      SNGLSGGLNGSKSFSETINYKQESYRTTIDRKTNHKSIGWGVEAHKIMNN 200
MRSA131              SNGLSGGLNGSKSFSETINYKQESYRTTIDRKTNHKSIGWGVEAHKIMNN 200
TCH_70               SNGLSGGLNGSKSFSETINYKQESYRTTIDRKTNHKSIGWGVEAHKIMNN 200
D30                  SNGLSGGLNGSKSFSETINYKQESYRTTIDRKTNHKSIGWGVEAHKIMNN 200
N315                 SNGLSGGLNGSKSFSETINYKQESYRTTIDRKTNHKSIGWGVEAHKIMNN 200
Mu50                 SNGLSGGLNGSKSFSETINYKQESYRTTIDRKTNHKSIGWGVEAHKIMNN 200
                     **************************************************

LukD Consensus Sequence SNGLSGGLNGSKSFSETINYKQESYRTTIDRKTNHKSIGWGVEAHKIMNN

Newman               GWGPYGRDSYDPTYGNELFLGGRQSSSNAGQNFLPTHQMPLLARGNFNPE 250
MW2                  GWGPYGRDSYDPTYGNELFLGGRQSSSNAGQNFLPTHQMPLLARGNFNPE 250
USA_300_FPR3757      GWGPYGRDSYDPTYGNELFLGGRQSSSNAGQNFLPTHQMPLLARGNFNPE 250
COL                  GWGPYGRDSYDPTYGNELFLGGRQSSSNAGQNFLPTHQMPLLARGNFNPE 250
USA_300_TCH1516      GWGPYGRDSYDPTYGNELFLGGRQSSSNAGQNFLPTHQMPLLARGNFNPE 250
MRSA131              GWGPYGRDSYDPTYGNELFLGGRQSSSNAGQNFLPTHQMPLLARGNFNPE 250
TCH_70               GWGPYGRDSYDPTYGNELFLGGRQSSSNAGQNFLPTHQMPLLARGNFNPE 250
D30                  GWGPYGRDSYDPTYGNELFLGGRQSSSNAGQNFLPTHQMPLLARGNFNPE 250
N315                 GWGPYGRDSYDPTYGNELFLGGRQSSSNAGQNFLPTHQMPLLARGNFNPE 250
Mu50                 GWGPYGRDSYDPTYGNELFLGGRQSSSNAGQNFLPTHQMPLLARGNFNPE 250
                     **************************************************

LukD Consensus Sequence GWGPYGRDSYDPTYGNELFLGGRQSSSNAGQNFLPTHQMPLLARGNFNPE

Newman               FISVLSHKQNDTKKSKIKVTYQREMDRYTNQWNRLHWVGNNYKNQNTVTF 300
MW2                  FISVLSHKQNDTKKSKIKVTYQREMDRYTNQWNRLHWVGNNYKNQNTVTF 300
USA_300_FPR3757      FISVLSHKQNDTKKSKIKVTYQREMDRYTNQWNRLHWVGNNYKNQNTVTF 300
COL                  FISVLSHKQNDTKKSKIKVTYQREMDRYTNQWNRLHWVGNNYKNQNTVTF 300
USA_300_TCH1516      FISVLSHKQNDTKKSKIKVTYQREMDRYTNQWNRLHWVGNNYKNQNTVTF 300
MRSA131              FISVLSHKQNDTKKSKIKVTYQREMDRYTNQWNRLHWVGNNYKNQNTVTF 300
TCH_70               FISVLSHKQNDTKKSKIKVTYQREMDRYTNQWNRLHWVGNNYKNQNTVTF 300
D30                  FISVLSHKQNDTKKSKIKVTYQREMDRYTNQWNRLHWVGNNYKNQNTVTF 300
N315                 FISVLSHKQNDTKKSKIKVTYQREMDRYTNQWNRLHWIGNNYKNQNTVTF 300
Mu50                 FISVLSHKQNDTKKSKIKVTYQREMDRYTNQWNRLHWIGNNYKNQNTVTF 300
                     *************************************:************

LukD Consensus Sequence FISVLSHKQNDTKKSKIKVTYQREMDRYTNQWNRLHWXGNNYKNQNTVTF

Newman               TSTYEVDWQNHTVKLIGTDSKETNPGV                         327
MW2                  TSTYEVDWQNHTVKLIGTDSKETNPGV                         327
USA_300_FPR3757      TSTYEVDWQNHTVKLIGTDSKETNPGV                         327
COL                  TSTYEVDWQNHTVKLIGTDSKETNPGV                         327
USA_300_TCH1516      TSTYEVDWQNHTVKLIGTDSKETNPGV                         327
MRSA131              TSTYEVDWQNHTVKLIGTDSKETNPGV                         327
TCH_70               TSTYEVDWQNHTVKLIGTDSKETNPGV                         327
D30                  TSTYEVDWQNHTVKLIGTDSKETNPGV                         327
N315                 TSTYEVDWQNHTVKLIGTDSKETNPGV                         327
Mu50                 TSTYEVDWQNHTVKLIGTDSKETNPGV                         327
                     **************************

LukD Consensus Sequence TSTYEVDWQNHTVKLIGTDSKETNPGV
```

→ Depicts the start of the secreted LukD protein

Thus, unless indicated to the contrary, both the immature and the mature forms of native LukE and LukD, and the sequences having less than 100% similarity with native LukE (i.e., native sequences and analogs alike, collectively referred to herein as "LukE" and "LukD") may be used in the methods of the present invention.

LukE and LukD proteins and polypeptides of the invention may differ from the native polypeptides designated as SEQ ID NOS:1-11 and 12-22 respectively, in terms of one or more additional amino acid insertions, substitutions or deletions, e.g., one or more amino acid residues within SEQ ID NOS: 1-22 may be substituted by another amino acid of a similar polarity, which acts as a functional equivalent, resulting in a silent alteration. That is to say, the change relative to the native sequence would not appreciably diminish the basic properties of native LukE or LukD. Any such analog of LukE or LukD may be screened in accordance with the protocols disclosed herein (e.g., the cell toxicity assay and the membrane damage assay) to determine if it maintains native LukE or LukD activity. Substitutions within these leukocidins may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

In other embodiments, non-conservative alterations (e.g., one or amino acid substitutions, deletions and/or additions) can be made for purposes of increasing the selectivity and/or activity of LukE and/or LukD. The modified LukE and LukD may be used in the therapeutic compositions described herein. Molecular alterations can be accomplished by methods well known in the art, including primer extension on a plasmid template using single stranded templates (Kunkel et al., *Proc. Acad. Sci., USA* 82:488-492 (1985), which is hereby incorporated by reference in its entirety), double stranded DNA templates (Papworth et al., *Strategies* 9(3):3-4 (1996), which is hereby incorporated by reference in its entirety), and by PCR cloning (Braman, J. (ed.), *IN VITRO MUTAGENESIS PROTOCOLS,* 2nd ed. Humana Press, Totowa, N.J. (2002), which is hereby incorporated by reference in its entirety). Methods of determining whether a given molecular alteration in LukE and LukD alters LukE/D cytotoxicity are described herein.

In a preferred embodiment of the present invention, a highly purified LukE/LukD preparation is utilized. Methods of purifying LukE and LukD toxins are known in the art (Gravet et al., "Characterization of a Novel Structural Member, LukE-LukD, of the Bi-Component Staphylococcal Leucotoxins Family," *FEBS* 436: 202-208 (1998), which is hereby incorporated by reference in its entirety). As used herein, "isolated" protein or polypeptide refers to a protein or polypeptide that has been separated from other proteins, lipids, and nucleic acids with which it is naturally associated with. Purity can be measured by any appropriate standard method, for example, by column chromatography, polyacrylamide gel electrophoresis, of HPLC analysis. An isolated protein or polypeptide of the invention can be purified from a natural source, produced by recombinant DNA techniques, or by chemical methods.

The therapeutic compositions of the present invention are prepared by formulating LukE and LukD with a pharmaceutically acceptable carrier and optionally a pharmaceutically acceptable excipient. As used herein, the terms "pharmaceutically acceptable carrier" and "pharmaceutically acceptable excipient" (e.g., additives such as diluents, immunostimulants, adjuvants, antioxidants, preservatives and solubilizing agents) are nontoxic to the cell or mammal being exposed thereto at the dosages and concentrations employed. Examples of pharmaceutically acceptable carriers include water, e.g., buffered with phosphate, citrate and another organic acid. Representative examples of pharmaceutically acceptable excipients that may be useful in the present invention include antioxidants such as ascorbic acid; low molecular weight (less than about 10 residues) polypeptides; proteins, such as serum albumin, gelatin, or immunoglobulins; adjuvants (selected so as to avoid adjuvant-induced toxicity, such as a β-glucan as described in U.S. Pat. No. 6,355,625 to Pavliak et al., which is hereby incorporated by reference in its entirety, or a granulocyte colony stimulating factor (GCSF)); hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

Therapeutic compositions of the present invention may be prepared for storage by mixing the active ingredient(s) having the desired degree of purity with the pharmaceutically acceptable carrier and optional excipient and/or additional active agent, in the form of lyophilized formulations or aqueous solutions.

Another aspect of the present invention relates to a method of preventing or treating Human Immunodeficiency Virus (HIV) infection in a subject. This method involves administering a composition comprising an isolated LukE protein, or polypeptide thereof, and an isolated LukD protein, or polypeptide thereof in an amount effective to prevent or treat HIV infection in the subject.

In accordance with this aspect of the invention a suitable composition for administration to a subject to treat HIV infection contains both LukE and LukD proteins or polypeptides that retain receptor binding and the cytotoxic function of the full-length LukE or LukD proteins. A suitable composition for administration to a subject to prevent HIV infection contains both LukE and LukD proteins or polypeptides that retain receptor binding functionality and retain cytotoxicity. In another embodiment of the present invention, LukE and LukD proteins retain receptor binding function but are not cytotoxic or have reduced cytotoxicity.

In accordance with this aspect of the invention, suitable LukE and LukD proteins and polypeptides include those described supra. This aspect of the invention is based on the applicants' discovery that LukE/D binds to the CCR5 receptor of leukocytes, which mediates HIV cell entry and infectivity. LukE/D binding to CCR5 mediates LukE/D cytotoxicity. Therefore, when treating a subject having HIV, LukE and LukD proteins or polypeptides of the composition bind to the CCR5 receptor and cause cell death of all HIV positive cells. This method of treatment is superior to current HIV therapeutic strategies because LukE/D treatment will selectively and specifically deplete all CCR5 positive, and therefore, all HIV positive cells in a subject.

When administering the LukE/D composition of the invention to prevent HIV infection in a subject, the LukE and LukD proteins or polypeptides are preferably modified to reduce cytotoxicity as described supra and/or to enhance LukE/LukD receptor binding. Accordingly, the composition may comprise a modified LukE or LukD protein or polypeptide that retains at least 70% sequence similarity to SEQ ID NOs: 11 and 22, respectively. Preferably, the LukE and LukD proteins or polypeptides of the invention retain at least 80% sequence similarity to SEQ ID NOs: 11 and 22, respectively. More preferably, the LukE and LukD proteins or polypeptides of the invention retain at least 90% sequence similarity to SEQ ID NOs: 11 and 22, respectively. Most preferably, the LukE and LukD proteins or polypeptides of the invention retain at least 95% sequence similarity to SEQ ID NOs: 11 and 22, respectively.

The therapeutic compositions of the present invention can be administered as part of a combination therapy in conjunction with another anti-HIV agent. Accordingly, the composition comprising an isolated LukE protein, or polypeptide thereof, and an isolated LukD protein, or polypeptide thereof may further comprise or be administered in combination with one or more antiviral or other agents useful in the treatment of HIV. Suitable antiviral agents include nucleoside reverse transcriptase inhibitors, non-nucleoside reverse transcriptase inhibitors and protease inhibitors. More specifically, suitable antiviral agents include, without limitation, zidovudine, lamivudine, zalcitabine, didanosine, stavudine, abacavir, adefovir dipivoxil, lobucavir, BC H-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 1 1607 and AG-1549.

For purposes of this and other aspects of the invention, the target "subject" encompasses any animal, preferably a mammal, more preferably a human. In the context of administering a composition of the invention for purposes of preventing HIV infection in a subject, the target subject encompasses any subject that is at risk for being infected by HIV. In the context of administering a composition of the invention for purposes of treating HIV infection in a subject, the target subject encompasses any subject infected with HIV.

In the context of using therapeutic compositions of the present invention to treat an HIV infection, a therapeutically effective amount of LukE and LukD is that amount capable of achieving a reduction in symptoms associated with infection, a decrease in the severity of at least one symptom, a decrease in the viral load of the subject, and preferably a complete eradication of the virus from the subject.

Therapeutically effective amounts of a LukE and LukD composition can be determined in accordance with standard procedures, which take numerous factors into account, including, for example, the concentrations of these active agents in the composition, the mode and frequency of administration, the severity of the HIV infection to be treated (or prevented), and subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer a composition containing LukE and LukD proteins or polypeptides, until a dosage is reached that provides the desired or required prophylactic or therapeutic effect. The progress of this therapy can be easily monitored by conventional assays.

Therapeutic compositions of the present invention may be administered in a single dose, or in accordance with a multi-dosing protocol. For example, in a multi-dosing protocol, the therapeutic composition may be administered once or twice daily, weekly, or monthly depending on the use and severity of the condition being treated. Different dosages, timing of dosages, and relative amounts of the therapeutic composition can be selected and adjusted by one of ordinary skill in the art. Modes of administration of the therapeutic compositions of the present invention are described infra.

Another aspect of the present invention relates to a method of preventing HIV infection of a subject. This method involves providing a composition comprising an isolated LukE protein, or polypeptide thereof, and an isolated LukD protein, or polypeptide thereof, and contacting the tissue of the subject with the composition under conditions effective to block HIV infectivity of cells in the tissue, thereby inhibiting HIV infection of the subject.

In accordance with this aspect of the invention, the composition comprising LukE and LukD serves as an anti-HIV microbicide, killing cells that are susceptible to HIV infection before infection occurs. The composition can be administered to any female or a male subject that is at risk for exposure to HIV as a prophylactic means of preventing HIV infection.

In accordance with this aspect of the invention, the LukE and LukD containing compositions of the present invention may further comprise one or more one or more additional agents. The one or more additional agents include, for example, and without limitation, a lubricant, an anti-microbial agent, an antioxidant, a humectant, an emulsifier, a spermicidal agent, or a mixture of two or more thereof.

Suitable lubricants include, without limitation, cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate or white wax, or a mixture of two or more thereof. Suitable antimicrobial agents include, without limitation, propylene glycol, methyl paraben or propyl paraben, or a mixture of two or more thereof. Suitable antioxidants include, without limitation, butylated hydroxyanisole, butylated hydroxytoluene, or edetate disodium, or a mixture of two or more thereof. Suitable humectants include, without limitation, ethylene glycol, glycerin, or sorbitol, or a mixture of two or more thereof. Suitable emulsifiers include, without limitation, carbomer, polyoxyethylene-10-stearyl ether, polyoxyethylene-20-stearyl ether, cetostearyl alcohol, cetyl alcohol, cholesterol, diglycol stearate, glyceryl monostearate, glyceryl stearate, hydroxypropyl cellulose, hydroxypropylmethyl cellulose, lanolin, polyoxyethylene lauryl ether, methyl cellulose, polyoxyethylene stearate, polysorbate, propylene glycol monostearate, sorbitan esters or stearic acid, or a mixture of two or more thereof.

In one embodiment of this aspect of the invention, the composition is formulated for topical application. Compositions for topical administration according to the present invention can be formulated as solutions, ointments, creams, foams, suspensions, lotions, powders, pastes, gels, sprays, aerosols, or oils for vaginal, anal, or buccal administration. In another embodiment of the invention, the composition is formulated for vaginal and/or rectal administration. In another embodiment of the invention, the composition is formulated for slow release from a vaginal device, such as a vaginal ring, an IUD, or a sponge, or other contraceptive device (e.g., condom). In yet another embodiment of the present invention, the composition is formulated for application as an oral rinse. In a preferred embodiment of the invention, the composition is applied or contacted directly with the skin or a mucous membrane of the subject.

Another aspect of the invention relates to a method of treating an inflammatory condition in a subject. This method involves administering a composition of the present invention comprising an isolated LukE protein, or polypeptide thereof, and an isolated LukD protein, or polypeptide thereof, in an amount effective to treat an inflammatory condition in the subject.

Applicants have discovered that LukE/D targets and kills human CCR5-positive leukocytes and that this LukE/D mediated cytotoxicity is substantially specific to these cells but not other nucleated mammalian cells. Since CCR5 is expressed in a subset of effector T cells that produce proinflammatory cytokines that are enriched locally during inflammation, compositions of the present invention comprising LukE and LukD proteins and polypeptides are useful in treating inflammatory conditions by depleting the CCR5 positive cell populations. Any subject, preferably a mammal, more preferably a human, can be treated in accordance with this aspect of the invention, regardless of the cause of the inflammation, e.g., any bacterial or viral infection. Suitable compositions containing LukE and LukD proteins and/or polypeptides are described supra.

The therapeutic compositions of the present invention may be used to treat a number of inflammatory conditions, including but not limited to acute inflammatory conditions, rheumatoid arthritis, Crohn's disease, atherosclerosis, psoriasis, ulcerative colitis, psoriatic arthritis, multiple sclerosis, lupus, type I diabetes, primary biliary cirrhosis, inflammatory bowel disease, tuberculosis, skin wounds and infections, tissue abscesses, folliculitis, osteomyelitis, pneumonia, scalded skin syndrome, septicemia, septic arthritis, myocarditis, endocarditis, toxic shock syndrome, allergic contact dermatitis, acute hypersensitivity, and acute neurological inflammatory injury (e.g., caused by acute infection).

Acute inflammatory conditions encompass the initial response of the body to invading stimuli, and involve the recruitment of plasma and white blood cells (leukocytes) to the localized area of the injured or infected tissues. Acute inflammatory conditions have a rapid onset and severe symptoms. The duration of the onset, from a normal condition of the patient to one in which symptoms of inflammation are seriously manifested, generally lasts up to about 72 hours. Acute inflammatory conditions that are amenable to treatment with the therapeutic compositions of the present invention include conjunctivitis, iritis, uveitis, central retinitis, external otitis, acute suppurative otitis media, mastoiditis, labyrinthitis, chronic rhinitis, acute rhinitis, sinusitis, pharyngitis, tonsillitis, contact dermatitis, dermonecrosis, diabetic polyneuritis, polymyositis, myositis ossificans, degenerative arthritis, rheumatoid arthritis, periarthritis scapulohumeralis, and osteitis deformans. In one embodiment of the present invention, the acute inflammatory condition is an infected wound in the skin or soft tissue.

In the context of treatment of an inflammatory condition, an effective amount of a LukE and LukD composition is the amount that is therapeutically effective in the sense that treatment is capable of achieving a reduction in the inflammation, a decrease in the severity of the inflammation, or even a total alleviation of the inflammatory condition.

The anti-inflammatory compositions of the present invention may be administered by any route of administration as described infra. In the case of treatment of acute inflammatory conditions that are localized, non-systemic administration may be preferred in which case the administration of the therapeutic composition is at or around the site of the acute inflammation. In this regard, compositions for topical administration are preferred. In addition to the topical formulations described supra, the topical formulation can also be in the form of patches or dressings impregnated with active ingredient(s), which can optionally comprise one or more excipients or diluents. In some embodiments, the topical formulation includes a material that enhances absorption or penetration of the active agent(s) through the skin or other affected areas.

A therapeutically effective amount of a LukE/LukD composition in accordance with this and other aspects of the invention is the amount necessary to obtain beneficial or desired results. A therapeutically effective amount can be administered in one or more administrations, applications or dosages and is not intended to be limited to a particular formulation or administration route.

Also in accordance with this aspect of the invention, the LukE/LukD composition can be administered in combination with other anti-inflammatory compositions, a TNFα inhibitor, or a combination thereof. Exemplary anti-inflammatory medications include, but are not limited to, non-steroidal anti-inflammatory drugs (NSAID), analgesics, glucocorticoids, disease-modifying anti-rheumatic drugs, dihydrofolate reductase inhibitors (e.g., methotrexate), biologic response modifiers, and any combination thereof.

A suitable NSAID is a selective cyclooxygenase-2 (COX-2) inhibitor. Exemplary COX-2 inhibitors include, without limitation, nimesulide, 4-hydroxynimesulide, flosulide, meloxicam, celecoxib, and Rofecoxib (Vioxx). Alternatively, a non-selective NSAID inhibitor is administered in combination with the LukE/D composition of the present invention. Exemplary non-selective NSAIDS inhibitors include, without limitation, diclofenac, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, salsalate, sulindac and tolmetin.

Preferred analgesics include, without limitation, acetaminophen, oxycodone, tramadol, and propoxyphene hydrochloride.

Preferred glucocorticoids include, without limitation, cortisone, dexamethosone, hydrocortisone, methylpredisolone, prednisolone, and prednisone.

Preferred biological response modifiers include a B-cell inhibitor, such as Rituximab, or a T cell activation inhibitor, such as, Leflunomide, Etanercept (Enbrel), or Infliximab (Remicade).

Suitable TNFα inhibitors include a TNF-α antibody, a matrix metalloproteinase inhibitor, a corticosteroid, a tetracycline TNFα antagonist, a fluoroquinolone TNFα antagonist, and a quinolone TNFα antagonist. Exemplary TNFα antagonist antibodies include, without limitation, infliximab, etanercept, CytoFAb, AGT-1, afelimomab, PassTNF, and CDP-870. Exemplary corticosteroids include, without limitation, mometasone, fluticasone, ciclesonide, budesonide, beclomethasone, beconase, flunisolide, deflazacort, betamethasone, methyl-prednisolone, dexamethasone, prednisolone, hydrocortisone, cortisol, triamcinolone, cortisone, corticosterone, dihydroxycortisone, beclomethasone dipropionate, and prednisone. Exemplary tetracycline TNF-α antagonists include, without limitation, doxycycline, minocycline, oxytetracycline, tetracycline, lymecycline, and 4-hydroxy-4-dimethylaminotetracycline.

Another aspect of the present invention relates to a method of preventing graft-versus-host-disease (GVHD) in a subject. This method involves administering a composition comprising an isolated LukE protein, or polypeptide thereof, and an isolated LukD protein, or polypeptide thereof, in an amount effective to prevent graft-versus-host-disease (GVHD) in the subject.

Graft-versus-host disease (GVHD) remains the primary complication of clinical bone marrow transplantation (BMT) and a major impediment to widespread application of this important therapeutic modality. The hallmark of GVHD is infiltration of donor T lymphocytes into host epithelial compartments of the skin, intestine, and biliary tract. GVHD occurs when mature T cells, contained in the bone marrow of the graft, are transplanted into immuno-suppressed hosts. After transplantation, host antigen presenting cells (APCs) activate T cells of the graft (donor T cells) by presenting host histocompatibility antigens to the graft T-cells. Donor-derived APCs may also activate donor T cells by cross-presenting host alloantigens. The newly generated host-specific T effector (hsTeff) populations then migrate to peripheral host organs and effect target organ damage GVHD generally occurs in an acute and chronic form. Acute GVHD will be observed within about the first 100 days post BMT, whereas chronic GVHD occurs after this initial 100 days. In addition to chronology, different clinical symptoms are also manifest in acute GVHD versus chronic GVHD. Acute GVHD is generally characterized by damage to host liver, skin, mucosa and intestinal epithelium in the host subject, although some forms of idiopathic pneumonia have also been reported. Chronic GVHD is, on the other hand, associated with damage to connective tissue as well as the organs and tissues damaged during acute GVHD in the host subject. In general, the methods of the present invention relate to therapies for either addressing GVHD that is already present in a host subject or preventing GVHD from arising in a host subject. In one embodiment, the present invention relates to methods of treating or preventing acute GVHD. In particular, the methods of the present invention are suitable for treating acute GVHD where the GVHD is damaging host intestinal epithelium. The methods of the present invention are also suitable for treating acute GVHD where the GVHD is damaging at least one tissue selected from the group consisting of the host liver, the host skin, the host lung and the host mucosa. Of course, the methods may be used to treat acute GVHD where the GVHD is damaging more than one tissue.

In accordance with this embodiment of the invention, CCR5-positive donor T cells transplanted into the recipient host during allogenic transplantation mediate GVHD. Accordingly, in one embodiment of the present invention, donor bone marrow cells are treated with a composition containing LukE and Luke D prior to transplantation to effectuate cell death of all CCR5$^+$ cells, thereby preventing GVDH.

In another embodiment of the present invention, treatment of the donor bone marrow cells is achieved by treating the graft. "Treating the graft" is intended to mean administering a composition or performing a procedure to the graft material, where the treatment is not intended to directly affect the host organism. Of course, successful treatment of the graft will indirectly affect the host organism in that the severity of GVHD may be reduced, or even removed entirely. The methods of the invention are not limited to the location of the graft at the time the graft is treated. Thus, in one embodiment, the graft is treated prior to removal from the donor organism. In another embodiment, the graft is treated after removal from the donor organism. In yet another embodiment, the graft is treated after removal from the donor organism, but prior to transplantation into the host subject. In still another embodiment, the graft is treated after transplantation into the host organism.

In accordance with this aspect of the invention, the composition comprising LukE and LukD may be administered as part of a combination therapy. For example, the LukE/D composition may be co-administered with another pharmaceutically active substance, such as but not limited to, methotrexate and cyclosporine. Additional agents that may be co-administered include but are not limited to, antibodies directed to various targets, tacrolimus, sirolimus, interferons, opioids, TNFα (tumor necrosis factor-α), binding proteins, Mycophenolate mofetil and other inhibitors of inosine monophosphate dehydrogenase (IMPDH), glucocorticoids, azathioprine and other cytostatic agents such as, but not limited to, antimetabolites and alkylating agents. In one embodiment, the graft or donor may be pretreated by administration of immunosuppressive drugs such as cyclosporine (alone or in combination with steroids) and methotrexate prior to transplantation. For prevention, immunosuppressive therapy typically consists of combined regimens of methotrexate (MTX), cyclosporin (CsA), tacrolimus (FK 506), and/or a corticosteriod. Intravenous gamma-globulin preparations administered prophylactically have also been shown to be beneficial for the prevention of GVHD. In addition, pentoxyfylline, a xanthine derivative capable of down-regulating TNFα production, may be administered with cyclosporin plus either methotrexate or methylprednisolone to further decrease incidence of GVHD. Chronic GVHD may be treated with steroids such as prednisone, ozothioprine and cyclosporine. Also, antithymocyte globulin (ATG) and/or Ursodiol may be used. Thalidomide with immunosuppressive properties has shown promising results in the treatment of chronic GVHD. Similar to thalidomide, clofazimine may also be coadministered with the composition of the present invention comprising LukE and LukD. Antibody targets for co-administered antibodies include, but are not limited to, T cell receptor (TCR), interleukin-2 (IL-2) and IL-2 receptors. Additionally, a CD(25) monoclonal antibody, anti-CD8 monoclonal antibody, or an anti-CD103 antibody may be co-administered for GVHD prophylaxis.

In accordance with this and all aspects of the present invention, composition of the present invention can be formulated for pharmaceutical use and administered by parenteral, topical, intravenous, oral, subcutaneous, intraperitoneal, intranasal, intramuscular, intra-arterial, intracranial, intradermal injection for prophylactic and/or therapeutic treatment.

When it is desirable to deliver the pharmaceutical compositions of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the pharmaceutical compositions may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The required dosage of the composition comprising LukE and LukD of the present invention depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery.

Another aspect of the present invention relates to a method of treating a *Staphylococcus aureus* infection in a subject. This method involves selecting a subject having a *S. aureus* infection and administering a composition comprising a CCR5 antagonist to the subject in an amount effective to treat the *S. aureus* infection in the subject.

For purposes of this aspect of the invention, the target subject encompasses any animal, preferably a mammal, more preferably a human that is infected and/or at risk to be infected with *S. aureus* or is at risk of *S. aureus* infection. Particularly suitable subjects include infants, juveniles, adults, and elderly adults, as well as immunocompromised individual. Additionally, suitable subjects include those subjects infected with methicillin-resistant *S. aureus* (MRSA) infection or methicillin sensitive *S. aureus* (MSSA) infection.

In accordance with this aspect of the invention, suitable CCR5 antagonists for inhibiting *S. aureus* LukE/D mediated cytotoxicity, thereby treating or preventing *S. aureus* infection are known in the art, and include, without limitation, maraviroc, vicriviroc, NCB-9471, PRO-140, CCR5 mAb004, 8-[4-(2-butoxyethoxy)phenyl]-1-isobutyl-N-[4-[[(1-propyl-1H-imadazol-5-yl-)methyl]sulphinyl]phenyl]-1, 2,3,4-tetrahydro-1-benzacocine-5-carboxamide, methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, methyl 3-endo-{8-[(3S)-3-(acetamido)-3-(3-fluorophenyl)propyl]-8-azabicyclo[3.2.-1]oct-3-yl}-2-methyl-4,5,6,7-tetrahydro-3H-imidazo[4,5-c]pyridine-5-carboxylate, ethyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, and N-{(1S)-3-[3-endo-(5-isobutyryl-2-methyl-4,5,6,7-tetrahydro-1H-imidazo[4,-5-c]pyridin-1-yl)-8-azabicyclo[3.2.1]oct-8-yl]-1-(3-fluorophenyl)propyl}acetamide).

Additional CCR5 antagonists and compositions containing the same are further described in U.S. Patent Publication No. 2007/0010509 to Shiota et al., and U.S. Pat. No. 7,625,905 to Lemoine et al., U.S. Pat. No. 6,476,062 to Chu et al., U.S. Pat. No. 7,728,135 to Shi et al., and U.S. Pat. No. 7,220,856 to Dunning et al., which are all hereby incorporated by reference in their entirety.

The CCR-5 antagonist can be administered as part of a combination therapy in conjunction with another active agent depending upon the nature of the *S. aureus* infection that is being treated. Such additional active agents include anti-infective agents, antibiotic agents, and antimicrobial agents. Representative anti-infective agents that may be useful in the present invention include vancomycin and lysostaphin. Other suitable anti-infective agents include agents that inhibit LukE/D mediated cytotoxicity (e.g., anti-LukE antibody, anti-LukD antibody, anti-LukE/D antibody).

Representative antibiotic agents and antimicrobial agents that may be useful in the present invention include penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. Dosages of these antibiotics are well known in the art. See, e.g., MERCK MANUAL OF DIAGNOSIS AND THERAPY, Section 13, Ch. 157, $100^{th}$ Ed. (Beers & Berkow, eds., 2004), which is hereby incorporated by reference in its entirety. The anti-inflammatory, anti-infective, antibiotic and/or antimicrobial agents may be combined prior to administration, or administered concurrently (as part of the same composition or by way of a different composition) or sequentially with the CCR5 antagonist composition of the present invention. In certain embodiments, the administering is repeated.

Compositions containing CCR-5 antagonists can be administered by parenteral, topical, intravenous, oral, subcutaneous, intraperitoneal, intranasal, intramuscular, intra-arterial, intracranial, or intradermal injections, for prophylactic and/or therapeutic treatment.

Another aspect of the present invention relates to a method of identifying a suitable treatment for a subjecting having a *S. aureus* infection. This method involves obtaining a sample from the subject and detecting or quantifying the level of CCR5 expression and CCR5 surface level in the sample. The method further involves comparing the detected level of CCR5 expression and CCR5 surface level in the sample to a control sample having a known or baseline CCR5 expression level and CCR5 surface level and determining a suitable treatment for the subject based on this comparison. The method further involves administering the determined suitable treatment to the subject.

In accordance with this aspect of the invention, individuals lacking CCR5 or having lower levels of CCR5 expression will be more resistant to infection with lukE/D+ *S. aureus* compared to individuals with higher levels of CCR5. Individuals having higher levels of CCR5 are more suitable candidates for treatment using a CCR5 receptor antagonist as described herein.

A further aspect of the present invention relates to a method of predicting severity of an *S. aureus* infection in a subject by monitoring CCR5 levels in the subject. This method involves isolating PBMCs from whole blood of the subject and performing flow cytometry analysis to determine CCR5 surface expression. The quantified amounts of surface CCR5 expression in the cells from the subject are compared to the amount of CCR5 in a control sample which produces little or undetectable amounts of CCR5 and control sample which produces high levels of CCR5 (e.g., Jurkat CCR5+) and the severity of the *S. aureus* infection is predicted based on CCR5 levels. High levels of CCR5 in the subject predict a more severe *S. aureus* infection, while lower levels of CCR5 in the subject predict a less severe infection. Methods of isolating and/or labeling PBMCs from a whole blood sample for FACs analysis are readily known in the art.

EXAMPLES

The following examples are provided to illustrate embodiments of the present invention but are by no means intended to limit its scope.

Example 1

LukE/D Significantly Contributes to *S. aureus* Pathogenesis

To test whether LukE/D plays a major role in the pathogenesis of *S. aureus* septicemic infection, a ΔlukE/D mutant in the MSSA strain Newman was constructed and the impact of the lukE/D deletion on virulence examined. Survival over time dramatically increased for mice infected with $10^7$ CFU of the ΔlukE/D mutant compared to that of mice infected with wild type (WT) *S. auerus*. All mice infected with WT *S. aureus* succumbed to infection by 250 hours. In contrast, nearly 100% of mice infected with ΔlukE/D mutant survived until at least 300 hours post infection, a phenotype fully complemented by introducing lukE/D into the ΔlukE/D mutant strain (ΔlukE/D::plukE/D; FIG. 1A). In addition, bacterial burden to the kidney was reduced by 10-fold compared to the WT or complemented strain (FIG. 1B). These results show that LukE/D is a critical virulence factor for *S. aureus* systemic infection. Thus LukE/D is an attractive novel target for development of new therapeutics to counter *S. aureus* infection.

Example 2

LukE/D Selectively Kills Human Immune Cell Lines

As described supra, LukE/D contributes to the pathogenesis of *S. aureus* mediated sepsis and systemic infection (FIGS. 1A-1B), indicating that inhibiting LukE/D could prove to be a novel mean by which to treat *S. aureus* infections.

Figures 2A, 2B:
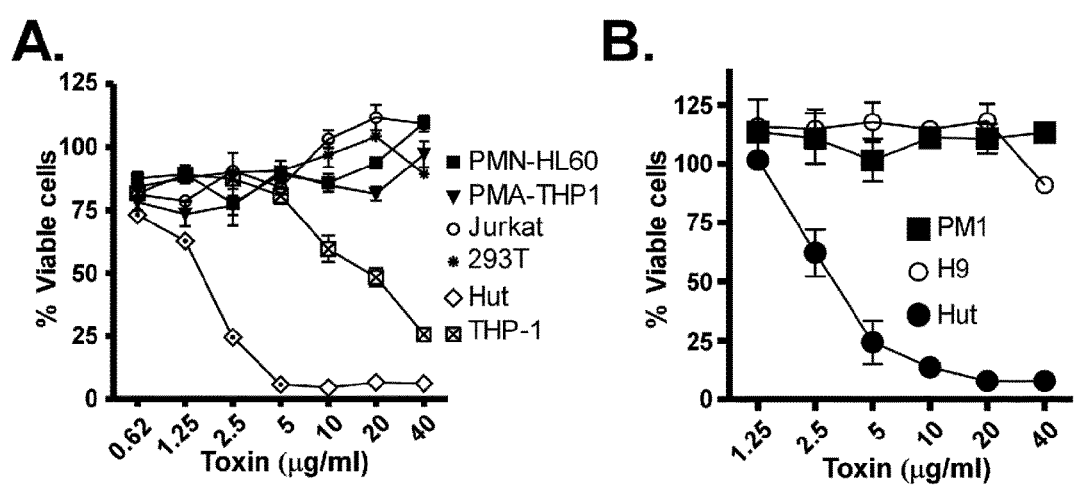
FIGS. 2A-2B show that LukE/D is toxic to select human immune cell lines.

One mechanism by which LukE/D could be blocked is by inhibiting the interaction of the toxin with its receptor. As an initial strategy to understand how LukE/D interact with host cells, a collection of human immune cell lines were incubated ("intoxicated") with different concentrations of either individual subunits (i.e., LukE or LukD) or an equimolar mixture of LukE+LukD (LukE/D). These experiments revealed that LukE/D exhibits cytotoxicity toward THP1 cells (human monocytes) and Hut cells (T lymphocyte-like cells) (FIG. 2A). Interestingly, LukE/D was cytotoxic towards Hut cells but not towards Jurkat cells, both commonly used T lymphocyte-like cells. This surprising result prompted investigation into what rendered the Hut cells sensitive to LukE/D. Intoxication of additional lymphocyte cell lines (PM1 and H9) revealed that only the Hut cells were susceptible to LukE/D mediated toxicity (FIG. 2B). Upon further investigation, it was discovered that the Hut cells employed the experiments described above have been engineered to over-express the CC-chemokine receptor 5 (CCR5), a receptor for the chemokines MIP-1α, MIP-1β, and RANTES.

Example 3

LukE/D Targets and Kills Cells in a CCR5-Dependent Manner

Figure 3:
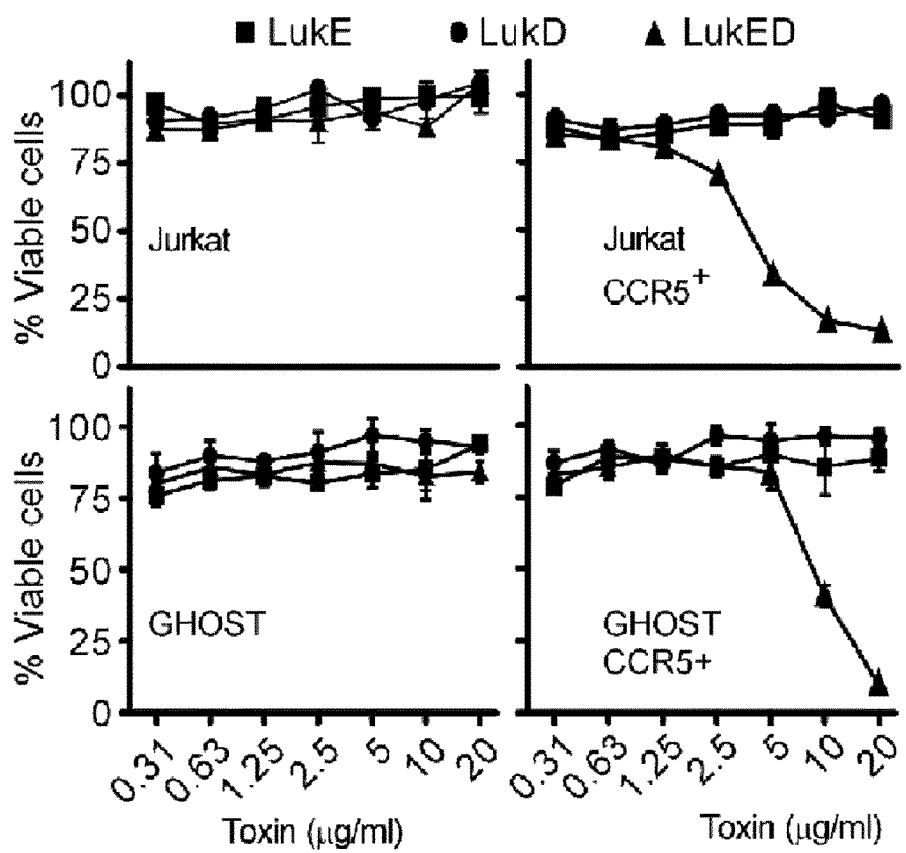
FIG. 3 illustrates that the chemokine receptor CCR5 is necessary and sufficient to renders mammalian cells susceptible to LukE/D mediated cytotoxicity. Parental Jurkat (top, left) and GHOST cells (bottom, left) or these cells transduced with a CCR5 cDNA (Jurkat CCR5+, top/right; GHOST CCR5+, bottom/right), were intoxicated with LukE, LukD, or equimolar mixture of LukE+LukD (LukE/D). One hour post-intoxication cell viability was monitored with CellTiter, where cells treated with medium were set at 100% viable. Results represent the average of triplicate samples ±S.D.

To directly determine the contribution of CCR5 for the ability of LukE/D to target and kill host cells, CCR5 was introduced into Jurkat cells by viral transduction of the CCR5 cDNA resulting in CCR5⁺ Jurkat. Jurkat and CCR5⁺ Jurkat cells were subsequently intoxicated with different concentrations of either individual subunits (i.e., LukE or LukD) or equimolar mixtures of LukE+LukD (LukE/D). This experiment revealed that production of CCR5 was sufficient to render Jurkat cells susceptible to LukE/D mediated toxicity (FIG. 3, top panel). Importantly, similar results were observed when the human osteosarcoma cell line "GHOST" cells engineered to produce CCR5 on their surface were examined (FIG. 3 bottom panel). Altogether, these data indicate that CCR5 renders mammalian cells susceptible to LukE/D mediated cytotoxicity.

Example 4

LukE/D Mediated Targeting of CCR5⁺ Cells is Blocked with Agonist, Antibodies and CCR5 Ligands CCR5 is a protein that has been highly studied because of its critical role in HIV-1 infection. Together with CD4, CCR5 is used by the virus to gain entry into cells. The importance of CCR5 to HIV pathogenesis in humans is best highlighted by the identification of subjects that have a mutation in the CCR5 gene (i.e., Δ32CCR5) that prevent the surface exposure of CCR5. Patients with this mutation are highly refractory to HIV infection. Currently, a variety of CCR5 antagonist (e.g., peptide mimetics, antibodies, small molecules) are being tested in clinical trials to be used as anti-HIV drugs as well as anti-inflammatory agents.

Figures 4A, 4B, 4C:
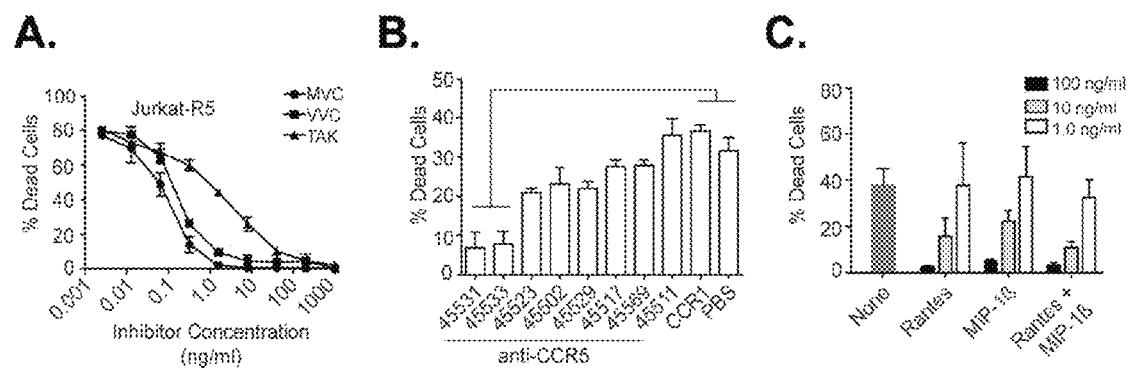
FIGS. 4A-4C show that LukE/D cytotoxicity towards host cells is blocked by CCR5 inhibitors.

To determine if targeting CCR5 blocks LukE/D, the effect of several CCR5 antagonist and ligands on the ability of LukE/D to kill CCR5 cells was evaluated. Among the CCR5 antagonist, the drugs Selzentry/Celsentri/Maraviroc (MVC), Vicriviroc (VVC) and TAK-779 (TAK) were tested for inhibition of LukE/D activity. CCR5⁺ Jurkat cells were pre-incubated with different concentrations of the antagonists, followed by intoxication with an equimolar mixture of LukE+LukD (LukE/D). These experiments indicated that all three CCR5 antagonists potently blocked LukE/D mediated cytotoxicity (FIG. 4A). In addition, the potential of monoclonal antibodies directed against CCR5 to protect cells from LukE/D cytotoxicity was also evaluated following the experimental protocol described for the CCR5 antagonist. These experiments also revealed that several of the tested monoclonal antibodies were indeed able to block LukE/D (FIG. 4B). Lastly, the potential inhibitory effect of natural ligands of CCR5 was also evaluated. CCR5⁺ Jurkat cells were pre-incubated with different concentrations of RANTES, MIP-1β, or a combination of equimolar mixture of RANTES+MIP-1β followed by intoxication with an equimolar mixture of LukE+LukD (LukE/D). These experiments also revealed that CCR5 ligands potently inhibit LukE/D cytotoxic effect (FIG. 4C). Collectively, these findings indicate that the potent cytotoxic activity of LukE/D could be blocked by employing CCR5 antagonist and/or ligands.

Example 5

Figures 5A, 5B, 5C:
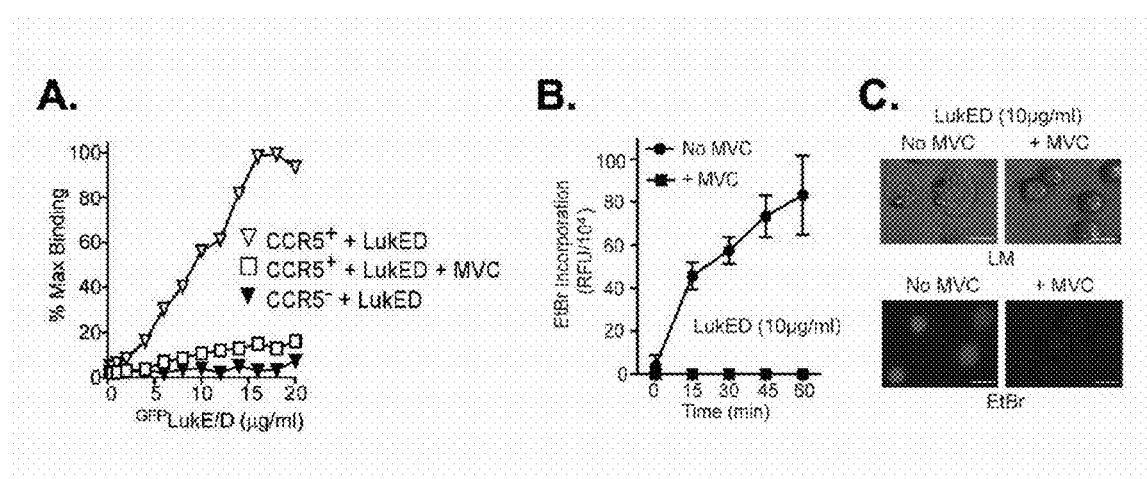
FIGS. 5A-5C illustrate that blocking LukE/D binding to the plasma membrane of target cells protects the cells from LukE/D mediated cytotoxicity.

Maraviroc Blocks LukE/D Binding to CCR5+ Cells Preventing the Formation of LukE/D Pores To elucidate the mechanism by which LukE/D utilizes CCR5 to target and kill host cells, Jurkat (CCR5−) and CCR5+ Jurkat (CCR5+) cells were incubated with a GFP-fused LukE/D toxin ($^{GFP}$LukE/D) and binding of the fluorescent toxin to the plasma membrane of the cells monitored by flow cytometry. These experiments revealed that LukE/D binds to CCR5+ Jurkat cells but not to the parental CCR5− Jurkat cells (FIG. 5A). To elucidate the mechanism by which Maraviroc inhibits LukE/D mediated cytotoxicity, CCR5+ Jurkat cells were pre-incubated with Maraviroc (MVC) followed by incubation with the GFP-labeled LukE/D toxin and toxin binding to the cells evaluated by flow cytometry. These experiments indicated that Maraviroc potently inhibited LukE/D binding to CCR5+ cells (FIG. 5A).

To examine the mechanism by which LukE/D is toxic to CCR5+ cells, cells were incubated in the presence or absence of Maraviroc and subsequently intoxicated with LukE/D in the presence of ethidium bromide, a small cationic dye that is normally impermeable to host cell membranes, but can gain access to host cells via the toxin pores. These experiments revealed that LukE/D forms pores in the plasma membrane of CCR5+ cells in a time-dependent manner. Importantly, Maraviroc (MVC) potently blocked LukE/D mediated pore formation (FIG. 5B). In addition, LukE/D pores were associated with cell swelling, a characteristic of cells intoxicated with leukotoxins, a phenotype fully blocked by Maraviroc (MVC) (FIG. 5C). Altogether, these findings indicate that LukE/D binds to host cells in a CCR5-dependent manner resulting in the formation of toxin mediated pores at the plasma membrane of target cells, leading to the observed LukE/D mediated cytotoxicity. Importantly, the CCR5 antagonist Maraviroc, potently inhibits LukE/D by blocking the interaction of LukE/D with the surface of CCR5+ cells, thus preventing pore formation and cell death.

Example 6

Figures 6A, 6B, 6C:
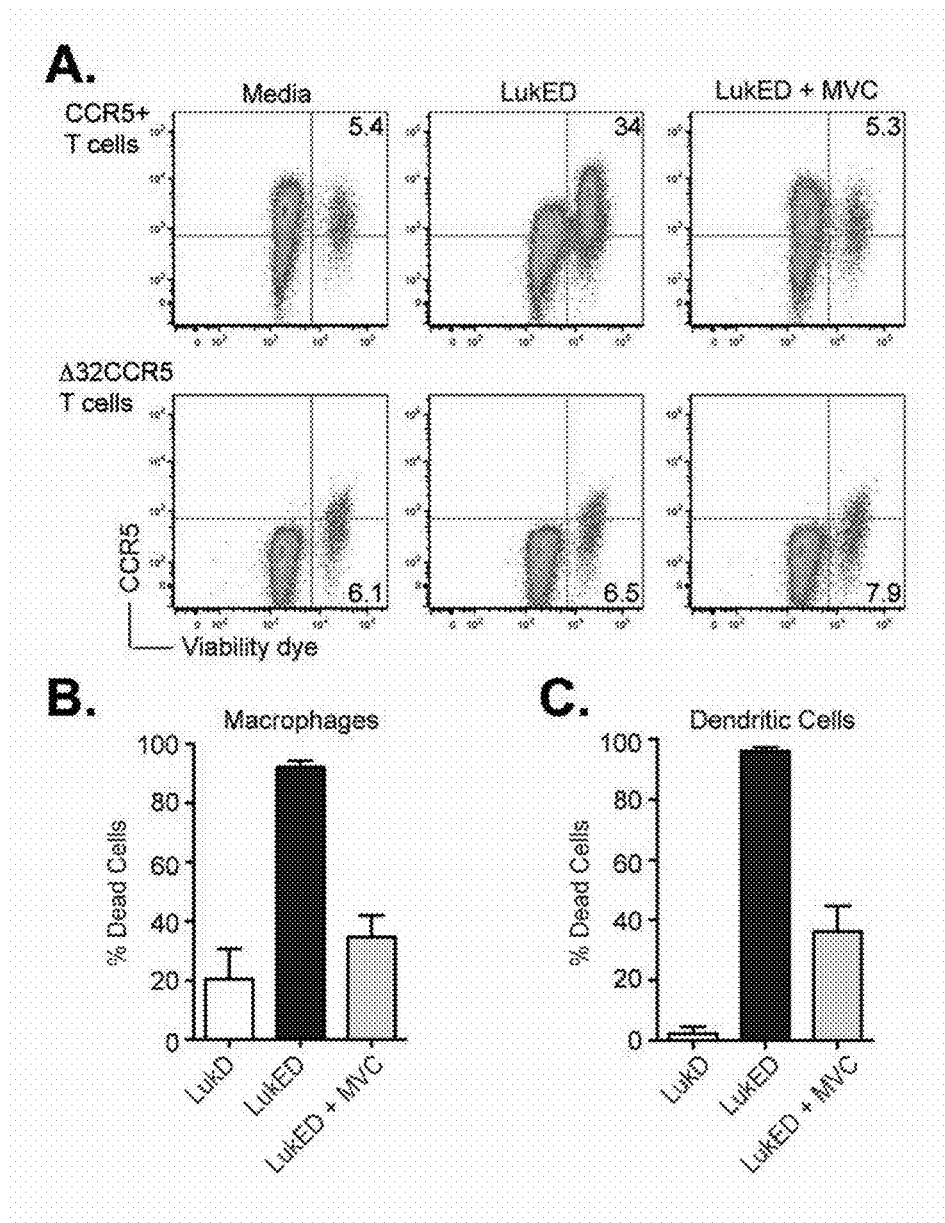
FIGS. 6A-C show that LukE/D potently kills CCR5+ primary human immune cells.

LukE/D Targets CCR5 to Kill Primary Human Lymphocytes, Macrophages, and Dendritic Cells If CCR5 is the receptor of LukE/D, then primary host cells that their surfaces are decorated with CCR5 (e.g., T lymphocytes, macrophages, natural killer cells, dendritic cells, etc.) will be susceptible to LukE/D mediated cell death. To investigate this in more detail, primary human peripheral blood mononuclear cells (PBMC) were isolated from a wild type CCR5 (CCR5+) donor and a Δ32CCR5 (CCR5−) donor and the T lymphocytes expanded followed by intoxication with LukE/D and the viability of the cells determined by flow cytometry. Primary human T lymphocytes from CCR5+ donor were highly susceptible to LukE/D (5.4% cell death in the media treated cells vs. 34% in LukE/D intoxicated cells; FIG. 6A, top panel), an effect potently neutralized by Maraviroc (LukE/D vs. LukE/D+MVC; FIG. 6A, top panel). In contrast, T lymphocytes from the Δ32CCR5 donor were highly refractory to LukE/D mediated cytotoxicity (FIG. 6A, bottom panel).

In addition to T lymphocytes, the cytotoxic activity of LukE/D towards primary human macrophages and dendritic cells was also evaluated. Macrophages and dendritic cells were incubated with LukD (negative control), intoxicated with an equimolar mixture of LukE+LukD (LukE/D), or incubated with Maraviroc (MVC) followed by intoxication with an equimolar mixture of LukE+LukD (LukE/D). LukE/D but not LukD potently killed both macrophages (FIG. 6B) and dendritic cells (FIG. 6C). Importantly, the cytotoxic effect of LukE/D towards these phagocytes was potently neutralized by Maraviroc (LukE/D vs. LukE/D+MVC; FIGS. 6B and 6C). Collectively, these data indicate that LukE/D targets and kills primary human leukocytes that harbor CCR5 at their surfaces, and that the CCR5 antagonist Maraviroc potently block LukE/D cytotoxic effects. Thus, blockade of LukE/D with CCR5 antagonist and/or inhibitors will offer a new therapeutic option to prevent and treat *S. aureus* infection.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of treating a *Staphylococcus aureus* infection in a subject, wherein *Staphylococcus aureus* expresses lukE/D comprising: selecting a subject with CCR5 expression and administering, to the selected subject, a composition comprising a CCR5 antagonist in an amount effective to treat the *S. aureus* infection in the subject.

2. The method of claim 1, wherein the CCR5 antagonist is maraviroc.

3. The method of claim 1 further comprising administering an agent selected from the group consisting of an anti-infective agent, an antibiotic agent, and an antimicrobial agent.

4. The method of claim 1, wherein the *Staphylococcus aureus* infection is a methicillin-resistant *Staphylococcus aureus* infection or methicillin-sensitive *Staphylococcus aureus* infection.

5. The method of claim 1 further comprising repeating said administering.

* * * * *